(12) United States Patent
Pollen et al.

(10) Patent No.: US 10,039,871 B2
(45) Date of Patent: Aug. 7, 2018

(54) MILK REPELLENT BREAST PUMP

(71) Applicants: Ashia M. Pollen, Madison, WI (US);
Robert J. Harter, La Crosse, WI (US)

(72) Inventors: Ashia M. Pollen, Madison, WI (US);
Robert J. Harter, La Crosse, WI (US)

( * ) Notice: Subject to any disclaimer, the term of this patent is extended or adjusted under 35 U.S.C. 154(b) by 605 days.

(21) Appl. No.: 14/685,677

(22) Filed: Apr. 14, 2015

(65) Prior Publication Data

US 2015/0217036 A1   Aug. 6, 2015

(51) Int. Cl.
*A61M 1/06* (2006.01)
*A61M 1/00* (2006.01)

(52) U.S. Cl.
CPC ............ *A61M 1/06* (2013.01); *A61M 1/0037* (2013.01); *A61M 1/0049* (2013.01); *A61M 1/064* (2014.02)

(58) Field of Classification Search
CPC ...... A61M 1/06; A61M 1/062; A61M 1/0037; A61M 1/0047; A61M 1/0049
See application file for complete search history.

(56) References Cited

U.S. PATENT DOCUMENTS

| | | | |
|---|---|---|---|
| 155,720 A | 10/1874 | Gray | |
| 684,078 A | 10/1901 | Martin | |
| 3,840,012 A | 10/1974 | Rushton, Jr. | |
| 4,263,912 A | 4/1981 | Adams | |
| 4,270,538 A | 6/1981 | Murphy | |
| 4,425,935 A | 1/1984 | Gonzalez | |
| 4,582,073 A | 4/1986 | Simkanich | |
| 4,673,388 A | 6/1987 | Schlensog et al. | |
| 4,857,051 A | 8/1989 | Larsson | |
| 4,892,517 A | 1/1990 | Yuan et al. | |
| 4,929,229 A | 5/1990 | Larsson | |
| 4,961,726 A * | 10/1990 | Richter | A61M 1/0037 604/313 |
| 5,009,638 A | 4/1991 | Riedweg et al. | |
| 5,071,403 A | 12/1991 | Larsson | |
| 5,295,957 A | 3/1994 | Aida et al. | |
| 5,358,476 A | 10/1994 | Wilson | |
| 5,571,084 A | 11/1996 | Palmer | |
| 5,720,722 A | 2/1998 | Lockridge | |
| 5,941,847 A | 8/1999 | Huber et al. | |
| 5,954,690 A | 9/1999 | Larsson | |
| 6,004,186 A | 12/1999 | Penny | |
| 6,379,327 B2 | 4/2002 | Lundy | |
| 6,440,100 B1 | 8/2002 | Prentiss | |
| 6,575,202 B2 | 6/2003 | Lafond | |
| 6,652,484 B1 | 11/2003 | Hunckler et al. | |
| 6,706,012 B2 | 3/2004 | McKendry et al. | |
| 6,764,377 B2 | 7/2004 | Gillan | |
| 6,821,185 B1 | 11/2004 | Francis | |
| 6,866,558 B2 | 3/2005 | Luciano et al. | |
| 6,887,217 B1 | 5/2005 | Logan | |

(Continued)

*Primary Examiner* — Nathan R Price
*Assistant Examiner* — Melissa A Snyder
(74) *Attorney, Agent, or Firm* — bobharter.com; Robert J. Harter

(57) ABSTRACT

A breast pump system includes a flexible vinyl suction tube that connects a milk collection device to a vacuum pump. If a milk droplet accidentally backflows into the suction tube, a supplementary opening injects tiny volumes of air sequentially into the vacuum pump or into the suction tube near the pump. As the vacuum pump operates in a cyclical manner, the injected air returns the droplet in sequential steps back to the milk collection device.

20 Claims, 22 Drawing Sheets

(56) References Cited

U.S. PATENT DOCUMENTS

| | | |
|---|---|---|
| 6,974,361 B2 | 12/2005 | Cravaack et al. |
| 7,094,217 B2 | 8/2006 | Fialkoff |
| 7,128,877 B2 | 10/2006 | Quay et al. |
| 7,223,255 B2 | 5/2007 | Myers et al. |
| 7,559,915 B2 | 7/2009 | Dao et al. |
| 8,075,516 B2 | 12/2011 | Pfenniger et al. |
| 8,118,772 B2 | 2/2012 | Dao et al. |
| 8,414,353 B1 | 4/2013 | Leavell |
| 8,529,501 B2 | 9/2013 | Wach et al. |
| 8,568,350 B2 | 10/2013 | Schlienger et al. |
| 8,702,646 B2* | 4/2014 | Garbez ................. A61M 1/064 604/74 |
| 8,801,495 B1 | 8/2014 | Guindon |
| 2004/0127845 A1* | 7/2004 | Renz ....................... A45C 3/06 604/74 |

\* cited by examiner

FIG. 7
FIG. 8
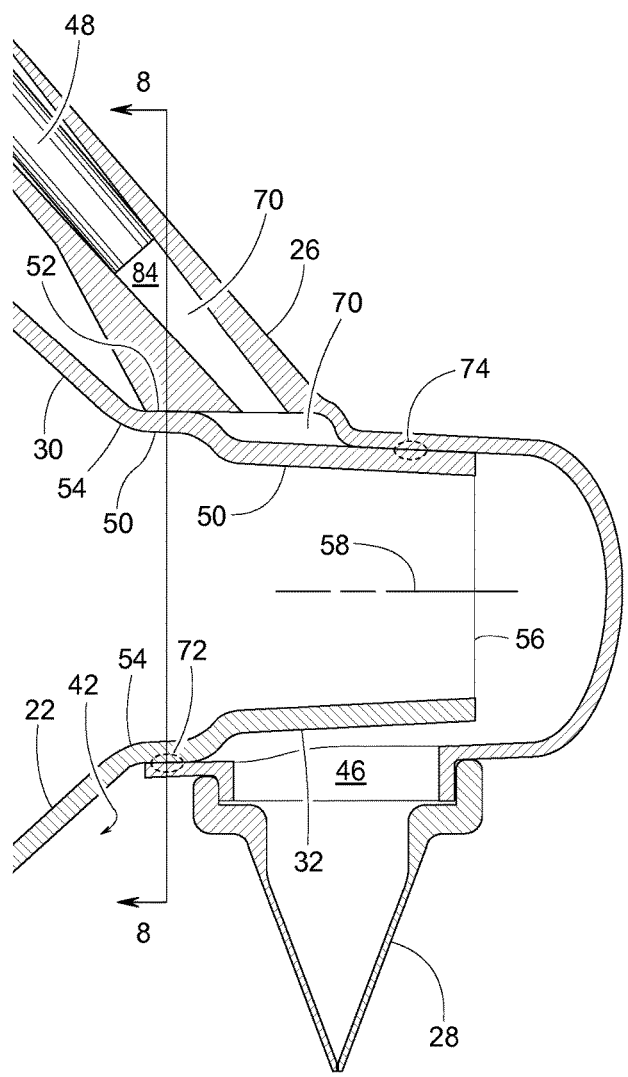
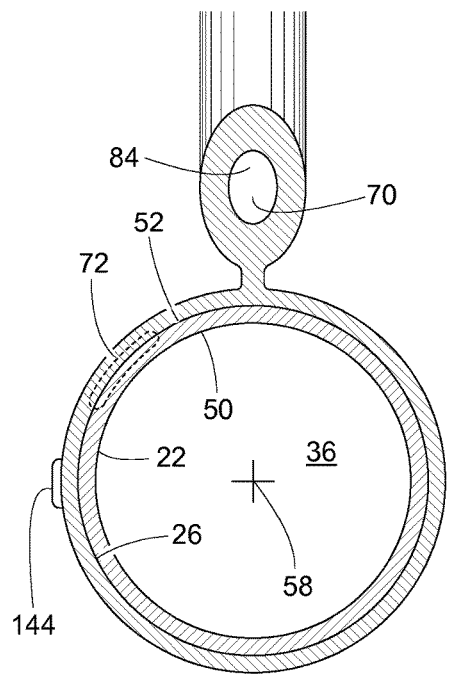

FIG. 9
FIG. 10
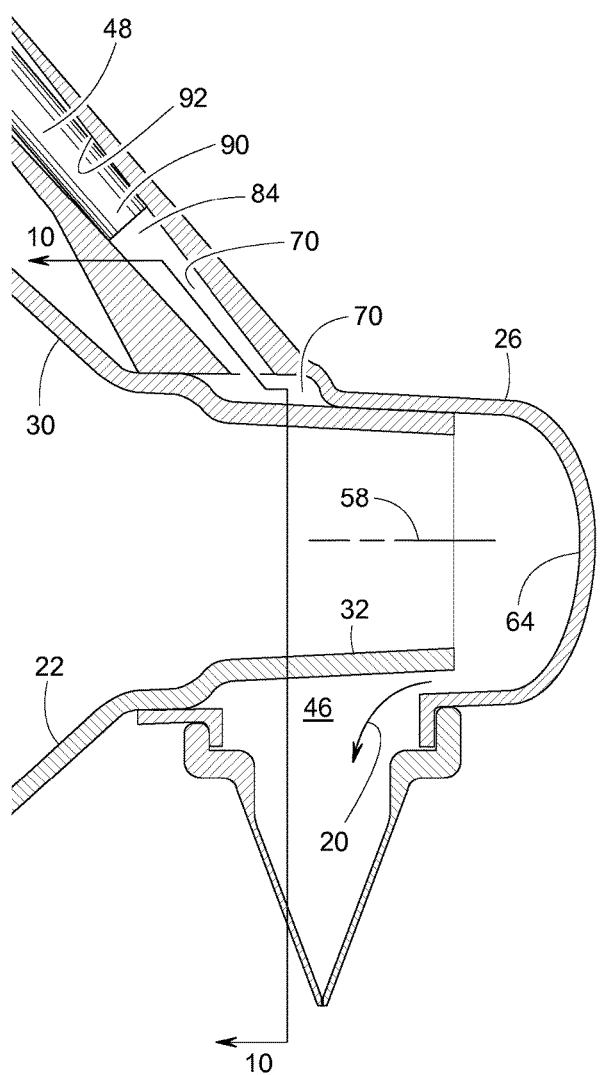
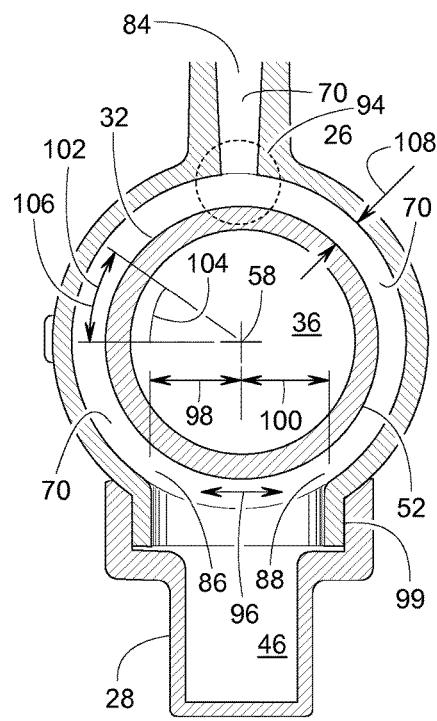

FIG. 11
FIG. 12
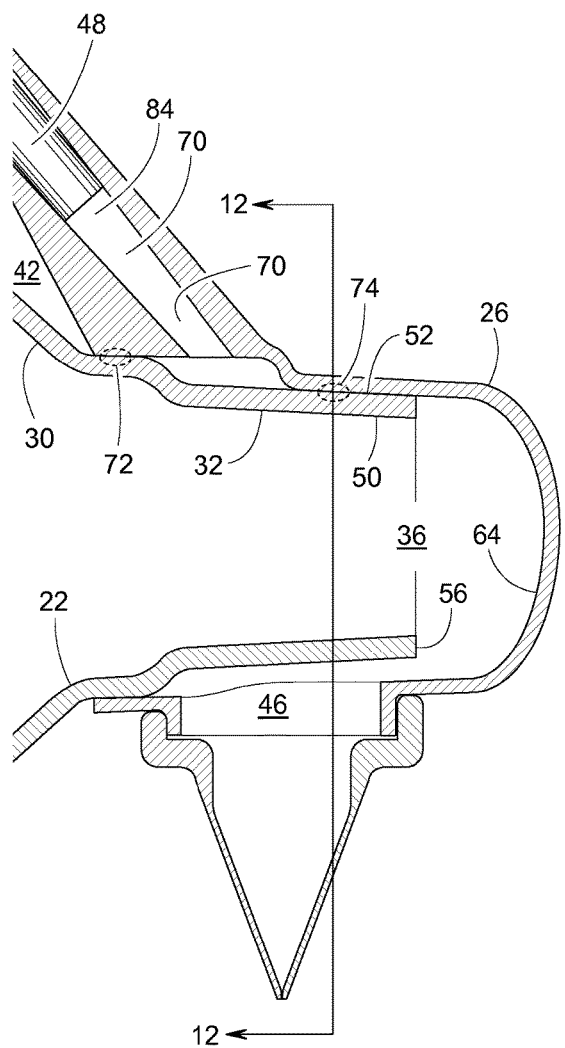
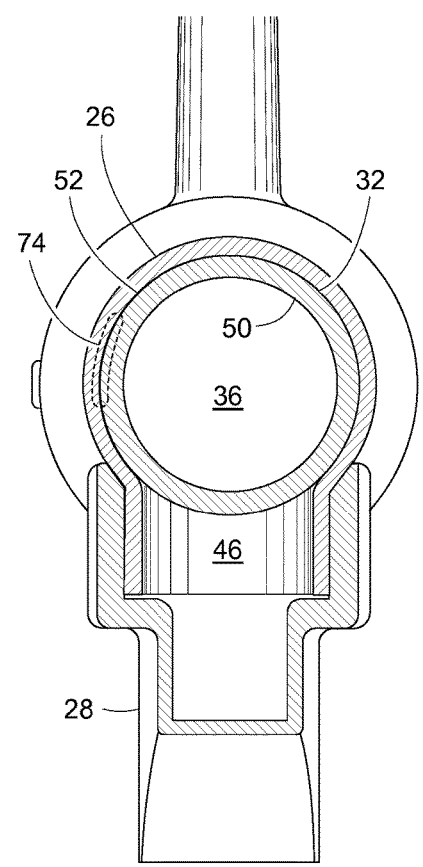

FIG. 13
FIG. 14
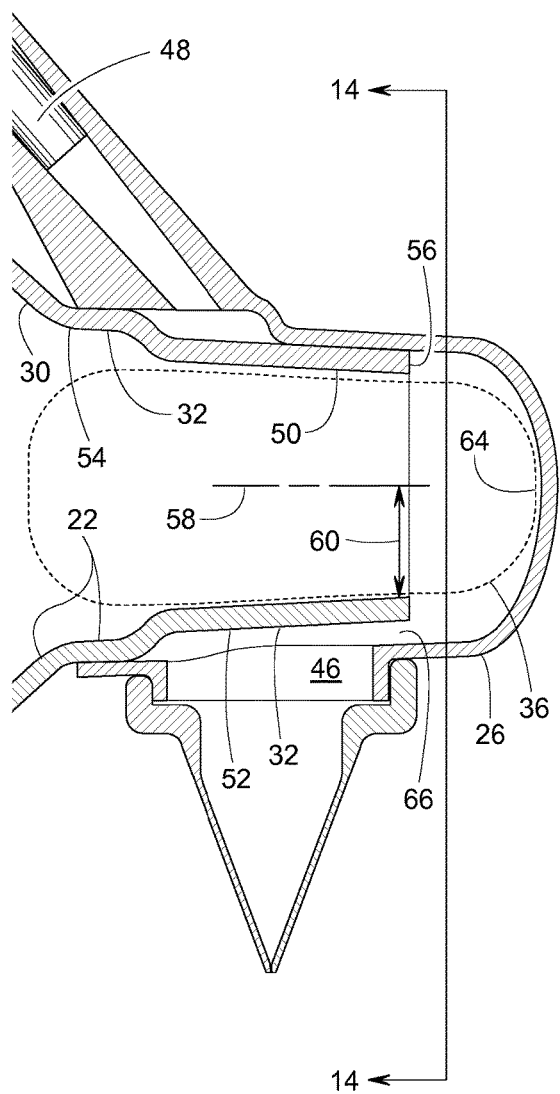
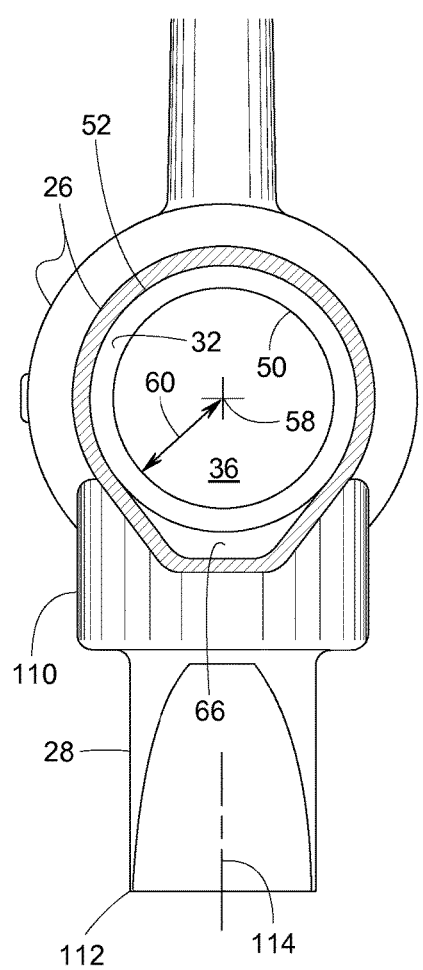

FIG. 15
FIG. 16
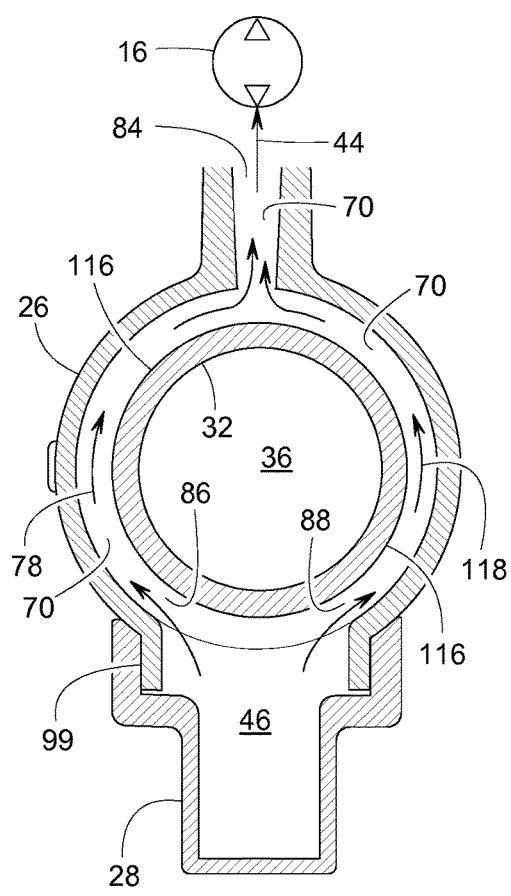
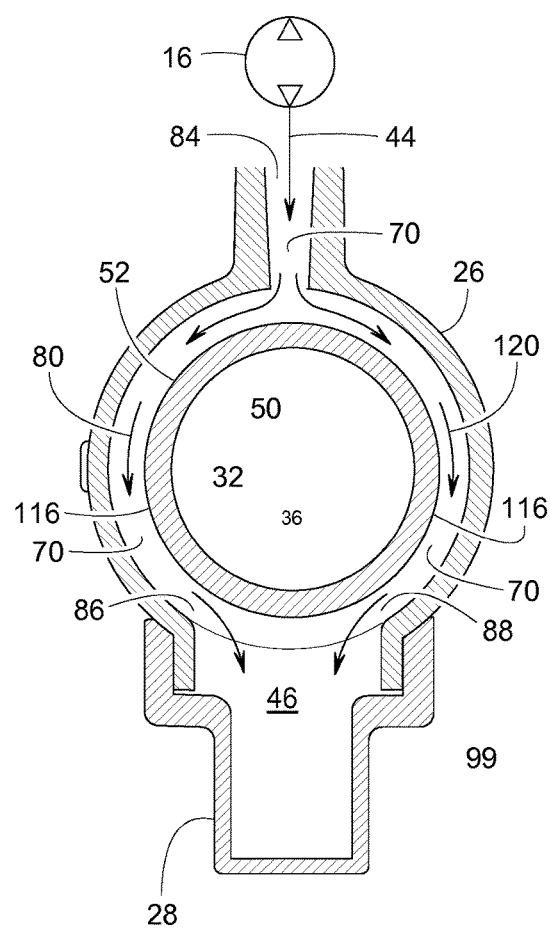

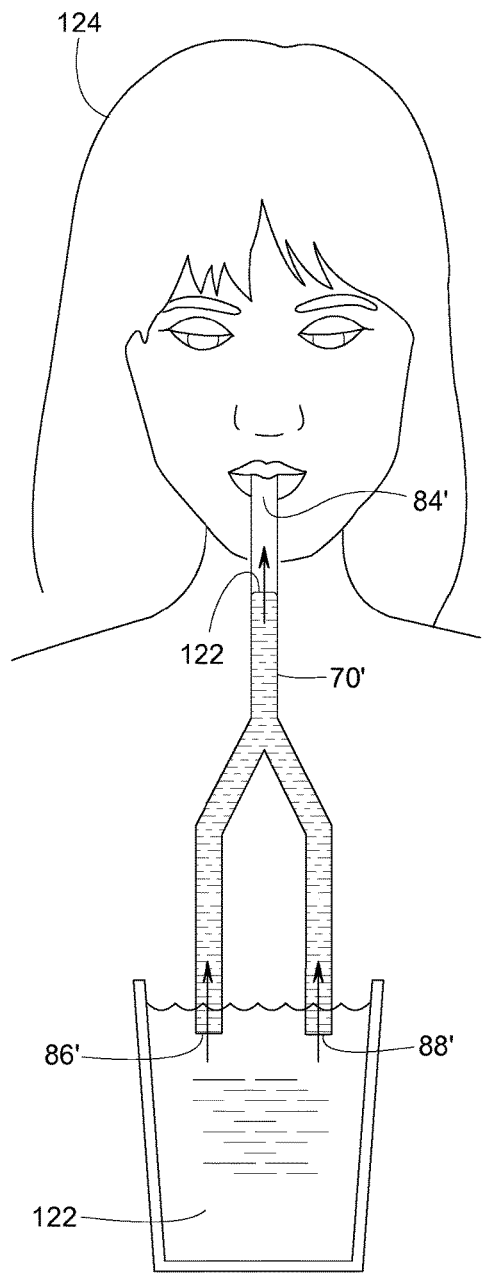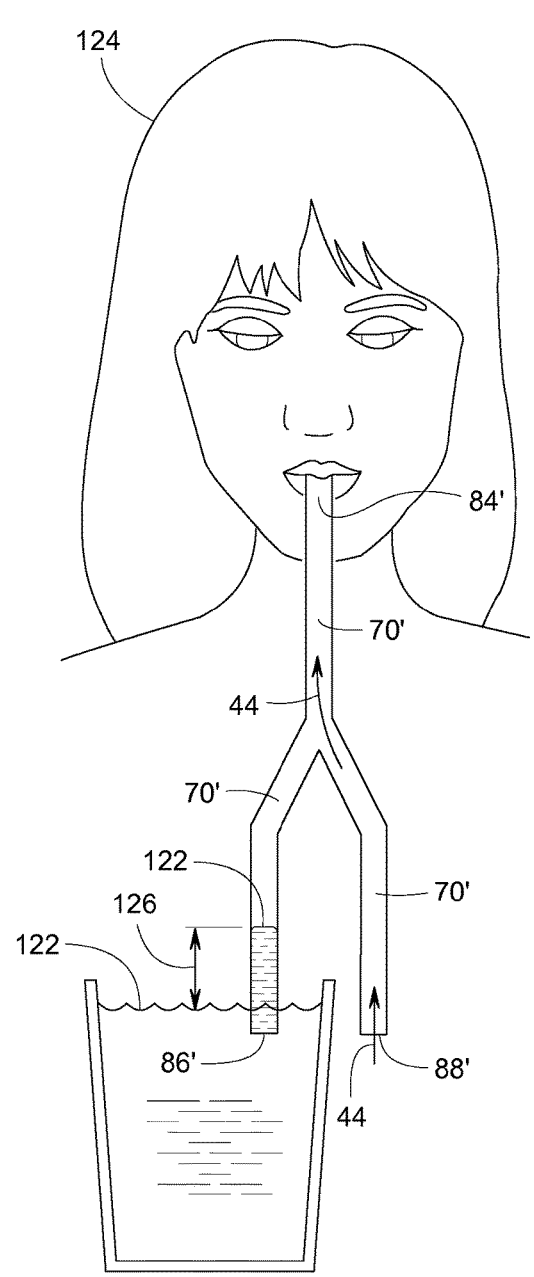

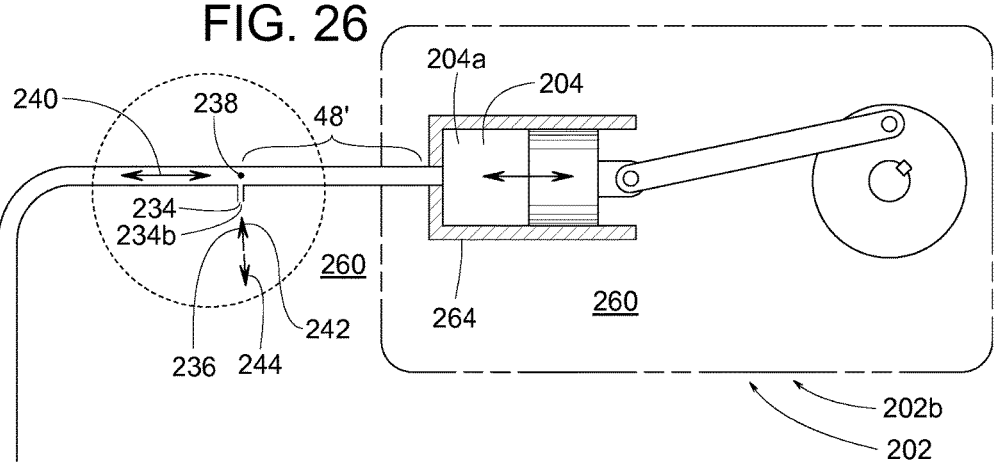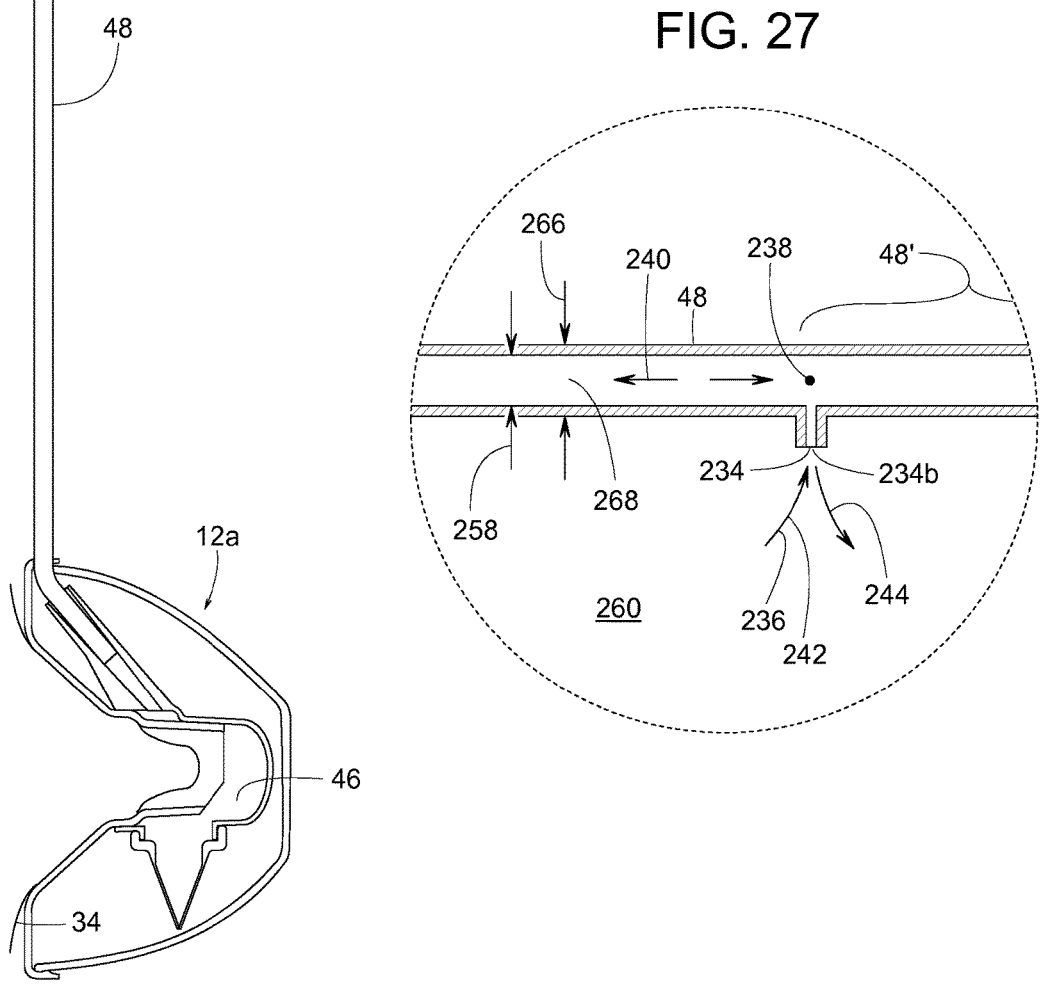

MILK REPELLENT BREAST PUMP

FIELD OF THE DISCLOSURE

The subject invention generally pertains to human breast milk collection systems and more specifically to means for inhibiting milk from backflowing through a suction tube to a vacuum pump.

BACKGROUND

Breast pump systems are used for collecting breast milk expressed from a lactating woman. Some breast pump systems have a milk collection device with a funnel that fittingly receives the woman's breast. In many cases, a vacuum pump provides cyclical periods of positive and negative pressure to the milk collection device. During periods of negative pressure (subatmospheric pressure), vacuum delivered to the device withdraws a small discrete volume of milk from the breast and conveys that charge of milk to a small charging chamber. During each period of positive pressure, lightly pressurized air relaxes the breast momentarily and at the same time forces the charge of milk from the charging chamber to a larger milk storage chamber. The cycle repeats until the storage chamber is full or the woman is finished "pumping."

Some breast pump systems have a milk collection device that is worn within the cup of a common brassiere. Examples of such systems are disclosed in U.S. Pat. Nos. 7,559,915; 8,118,772; and 8,702,646; all of which are incorporated herein by reference. Other breast pump systems have funnels that are handheld or are supported by or extend through a special purpose brassier. Examples of such systems are disclosed in U.S. Pat. Nos. 5,941,847; 7,094,217; and 8,057,452; all of which are incorporated herein by reference.

BRIEF DESCRIPTION OF THE DRAWINGS

FIG. 7 is a cross-sectional view showing a portion of FIG. 6.

FIG. 8 is a cross-sectional view taken along line 8-8 of FIG. 7.

FIG. 9 is a cross-sectional view showing a portion of FIG. 6.

FIG. 10 is a cross-sectional view taken along line 10-10 of FIG. 9.

FIG. 11 is a cross-sectional view showing a portion of FIG. 6.

FIG. 12 is a cross-sectional view taken along line 12-12 of FIG. 11.

FIG. 13 is a cross-sectional view showing a portion of FIG. 6.

FIG. 14 is a cross-sectional view taken along line 14-14 of FIG. 13.

FIG. 15 is a cross-sectional view similar to FIG. 10 but showing an airflow pattern during a negative pressure period (first period).

FIG. 16 is a cross-sectional view similar to FIG. 15 but showing an airflow pattern during a positive pressure period (second period).

FIGS. 17 and 18 are illustrations demonstrating an example "vacuum break" concept.

FIG. 26 is a combination schematic diagram and cross-sectional side view similar to FIGS. 23 and 24 but another example breast pump system constructed in accordance with the teachings disclosed herein.

FIG. 27 is an enlarged view of area 27 in FIG. 26.

DETAILED DESCRIPTION

Figure 19:
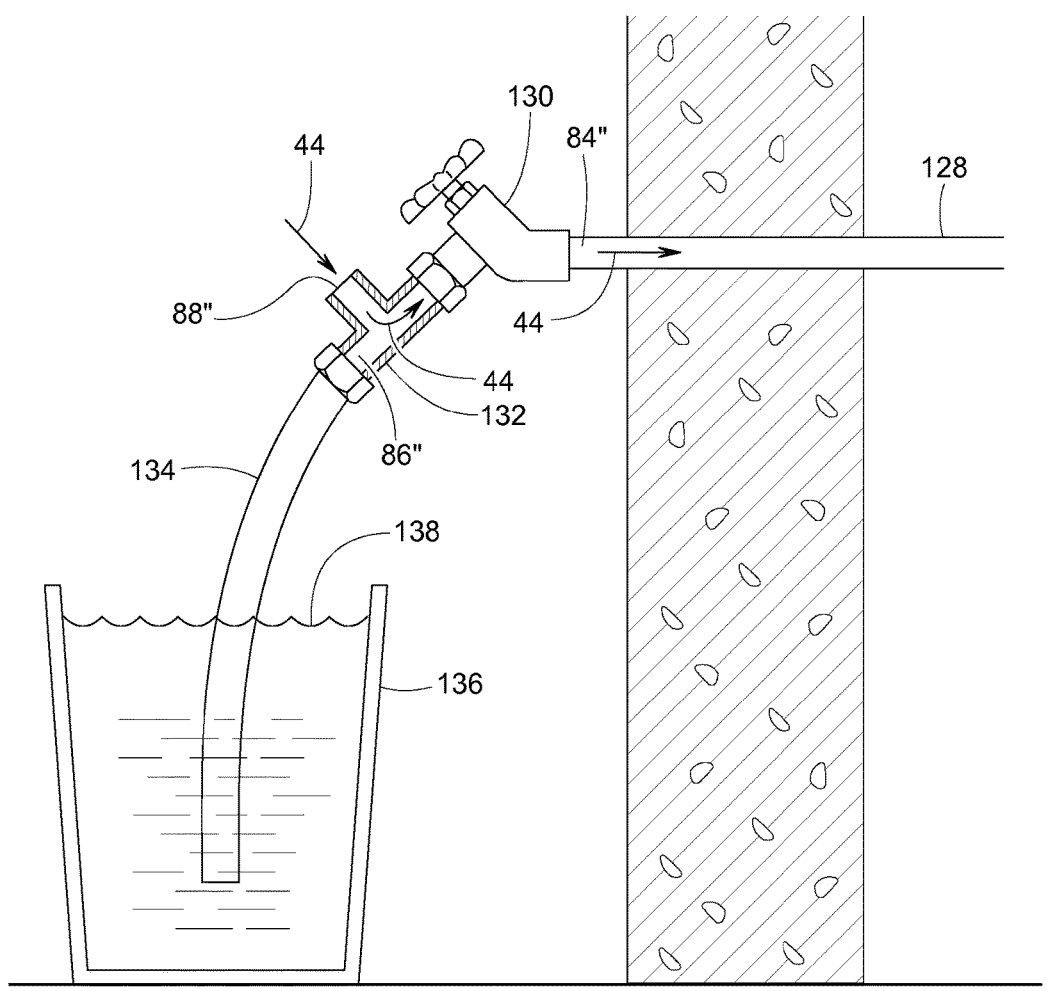
FIG. 19 is an illustration demonstrating another example "vacuum break" concept.
Figure 21:
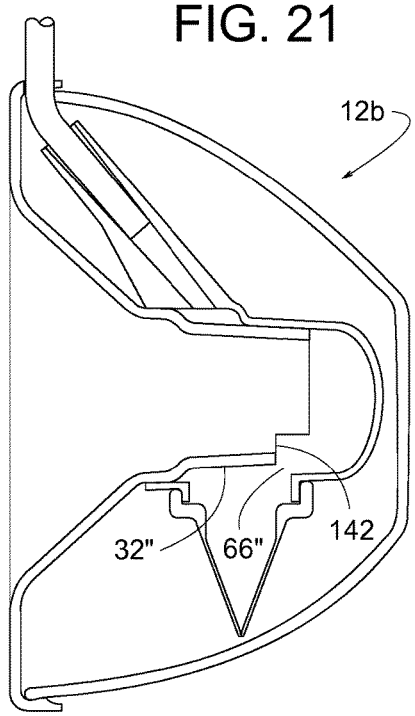
FIG. 21 is a cross-sectional view similar to FIG. 1 but showing another example milk collection device constructed in accordance with the teachings disclosed herein.
Figure 22:
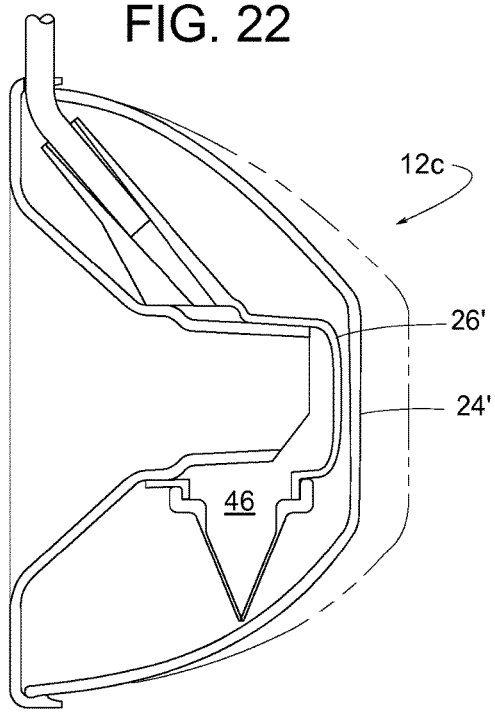
FIG. 22 is a cross-sectional view similar to FIG. 1 but showing of another example milk collection device constructed in accordance with the teachings disclosed herein.

FIGS. 1-16 show various views of an example breast pump system 10 that includes a milk collection device 12 with means for preventing milk 14 from backflowing to a vacuum pump 16. FIGS. 17-19 illustrate the underlying operating principle of vacuum breakers. And FIGS. 21-22 show variations of the system design. The general design isolates a subatmospheric air flow path 102 (FIG. 10) from a milk flow path 20 (FIG. 9) even if milk collection device 12 it tipped completely over (FIG. 4). The vacuum breaker concept keeps fluids separated without using conventional baffles, which inherently have crevices that can be difficult to clean.

Figure 1:
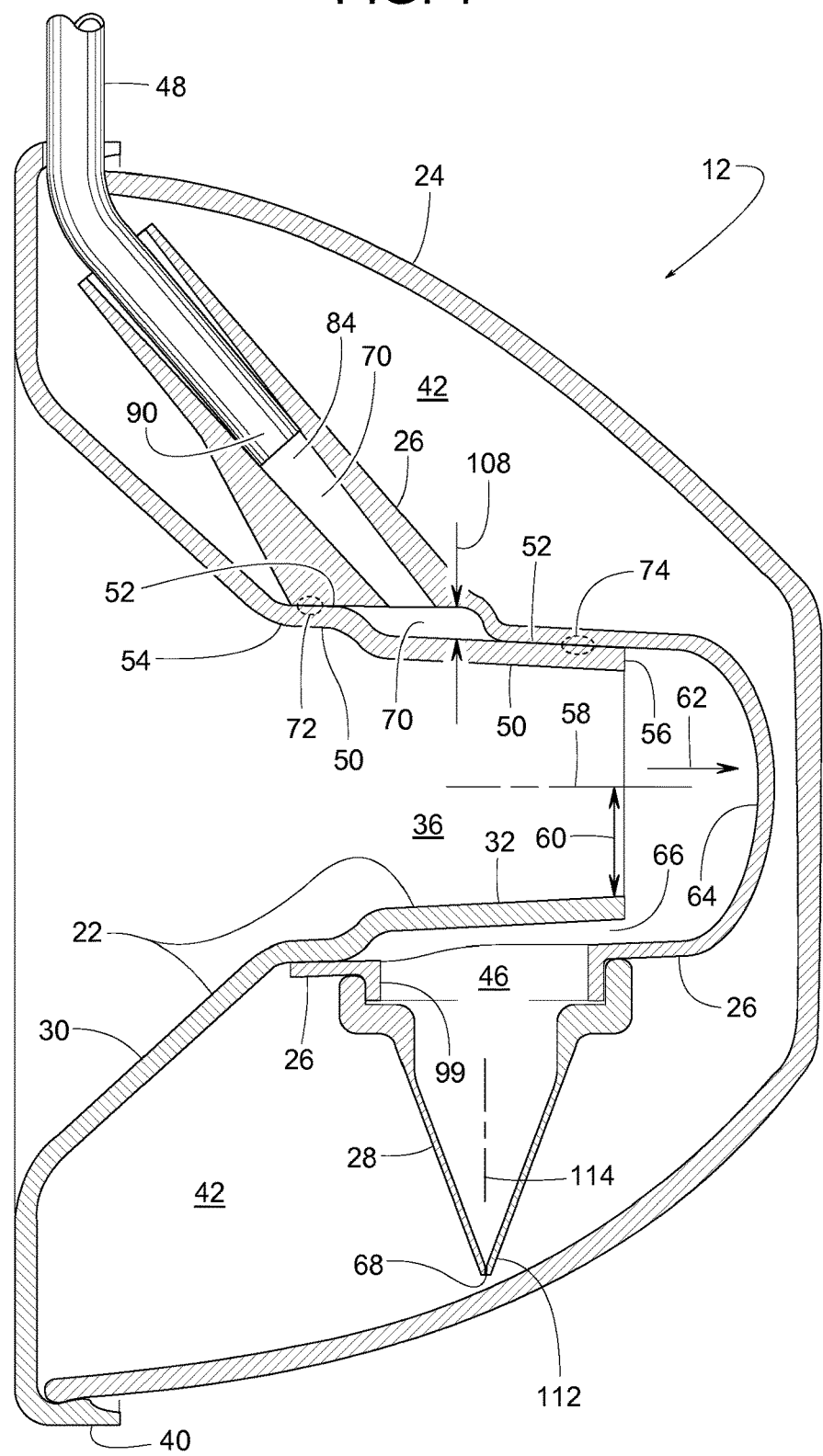
FIG. 1 is a cross-sectional side view of an example milk collection device constructed in accordance with the teachings disclosed herein.
Figure 5:
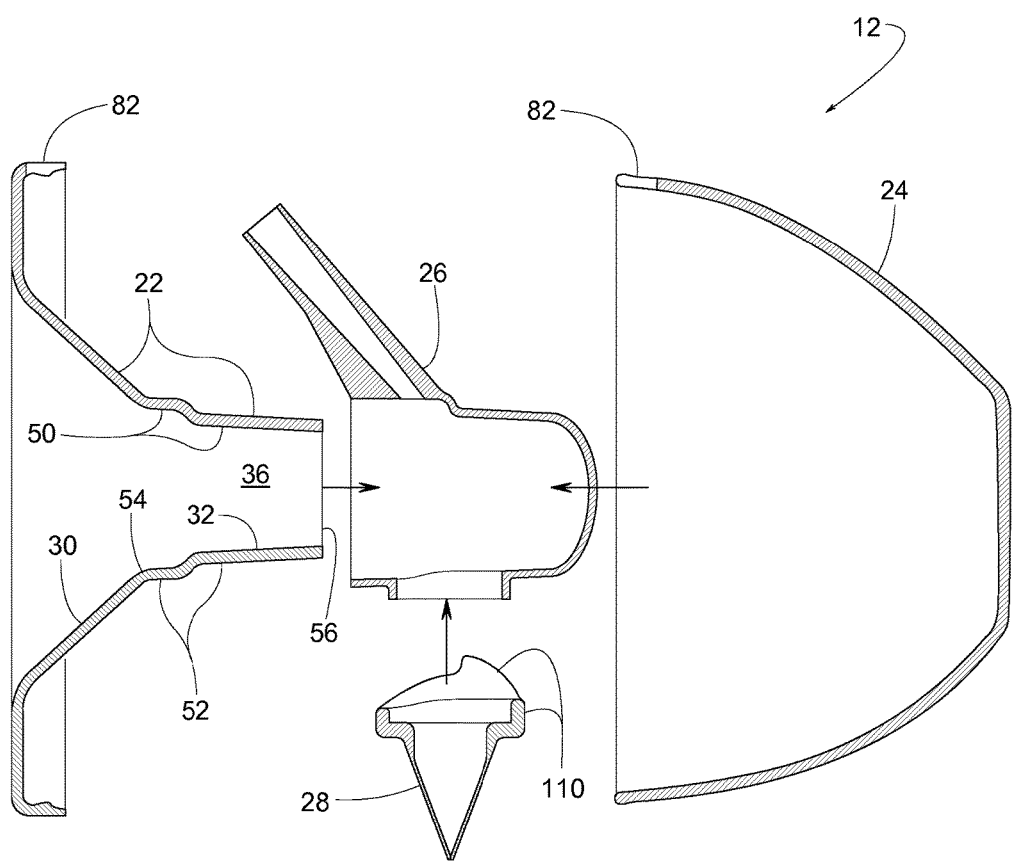
FIG. 5 is a cross-sectional view of the milk collection device shown in FIG. 1 but showing the device in a disassembled cleaning state.

As an overview of the breast pump system's general construction, milk collection device 12 comprises four main parts: a funnel-shaped breast receiver 22, a domed outer shell 24, a fluid exchanger 26, and a unidirectional valve 28 (e.g., a check valve, a duckbill check valve, a reed valve, a ball check valve, a diaphragm check valve, a swing check valve, etc.). FIG. 1 shows these for main parts in an assembled operating state with the parts being positioned as a unit in a predetermined orientation, and FIG. 5 shows them in a disassembled cleaning state. Breast receiver 22 itself comprises a breast guide 30 and a nipple receptacle 32. Breast guide 30 is generally conical for fittingly receiving a breast 34 of a lactating woman 36, and nipple receptacle 32 is tubular and defines a nipple chamber 36 for receiving a nipple 38 of breast 34.

In some examples, outer shell 24 removably connects to a flange 40 of breast receiver 22 to define a milk storage chamber 42 between outer shell 24 and breast receiver 22. Fluid exchanger 26 is coupled to breast receiver 22 to provide means for strategically directing milk 14 and air 44 within milk collection device 12. Valve 28 establishes a milk charging chamber 46 between nipple receptacle 36 and storage chamber 42. In some examples, charging chamber 46 is cycled between positive and negative pressure to draw discrete quantities of expressed milk from nipple receptacle 36. During periods of positive pressure, charging chamber 46 discharges each discrete quantity or charge through valve 28 to storage chamber 42.

To provide charging chamber 46 with air 44 cyclically at subatmospheric pressure and positive or atmospheric pressure, a suction tube 48 couples milk collection device 12 to vacuum pump 16. The term, "vacuum pump," refers to any device that provides subatmospheric pressure continuously, cyclically, or at least momentarily. Vacuum pump 16 is schematically illustrated to represent all types of vacuum pumps, examples of which include, but are not limited to, a diaphragm pump, a bellows pump, a piston pump, a reciprocating pump, a peristaltic pump, a positive displacement pump, a gear pump, a lobed rotor pump, a screw compressor, a scroll compressor, and a rotary vane pump.

The breast pump system's structure and operation can be further understood with additional definitions and explanations of some detailed features of the system. Nipple receptacle 36 has an inner curved wall surface 50, an outer curved wall surface 52, a proximate end 54 and a distal end 56. The nipple receptacle's tubular shape defines a longitudinal centerline 58 and nipple chamber 30. A minimum radial distance 60 exists between longitudinal centerline 58 and inner curved wall surface 50, wherein the minimum radial distance is measured perpendicular to centerline 58. Nipple receptacle 36 extends longitudinally in a forward direction 62 (parallel to centerline 58) from proximate end 54 to distal end 56. In some examples, nipple chamber 36 extends farther forward than distal end 56 of nipple receptacle 32; however, any part of nipple receptacle 32 that happens to extend farther forward than nipple chamber 36 is considered an extension beyond distal end 56 and thus is not considered the receptacle's distal end 56 itself. In some examples, the most forward point of nipple chamber 36 is at a domed concave surface 64 on fluid exchanger 26. Surface 64 being domed rather than flat makes fluid exchanger 26 easier to clean after fluid exchanger 26 is separated from breast receiver 22.

When breast receiver 22 and valve 28 are attached to fluid exchanger 26, the resulting assembly produces various fluid passages, chambers and sealing interfaces. Upon disassembly, the passages, chambers and sealing interfaces become more open for easier cleaning and sanitizing. Examples of such passages, chambers and sealing interfaces include charging chamber 46, nipple chamber 36, a milk passage 66 for conveying milk 14 from nipple chamber 36 to charging chamber 46, a valve outlet 68 that periodically discharges discrete volumes of milk 14 to storage chamber 42, an air duct 70 that connects suction tube 48 in fluid communication with charging chamber 46, a primary sealing interface 72, and a secondary sealing interface 74.

Figure 2:
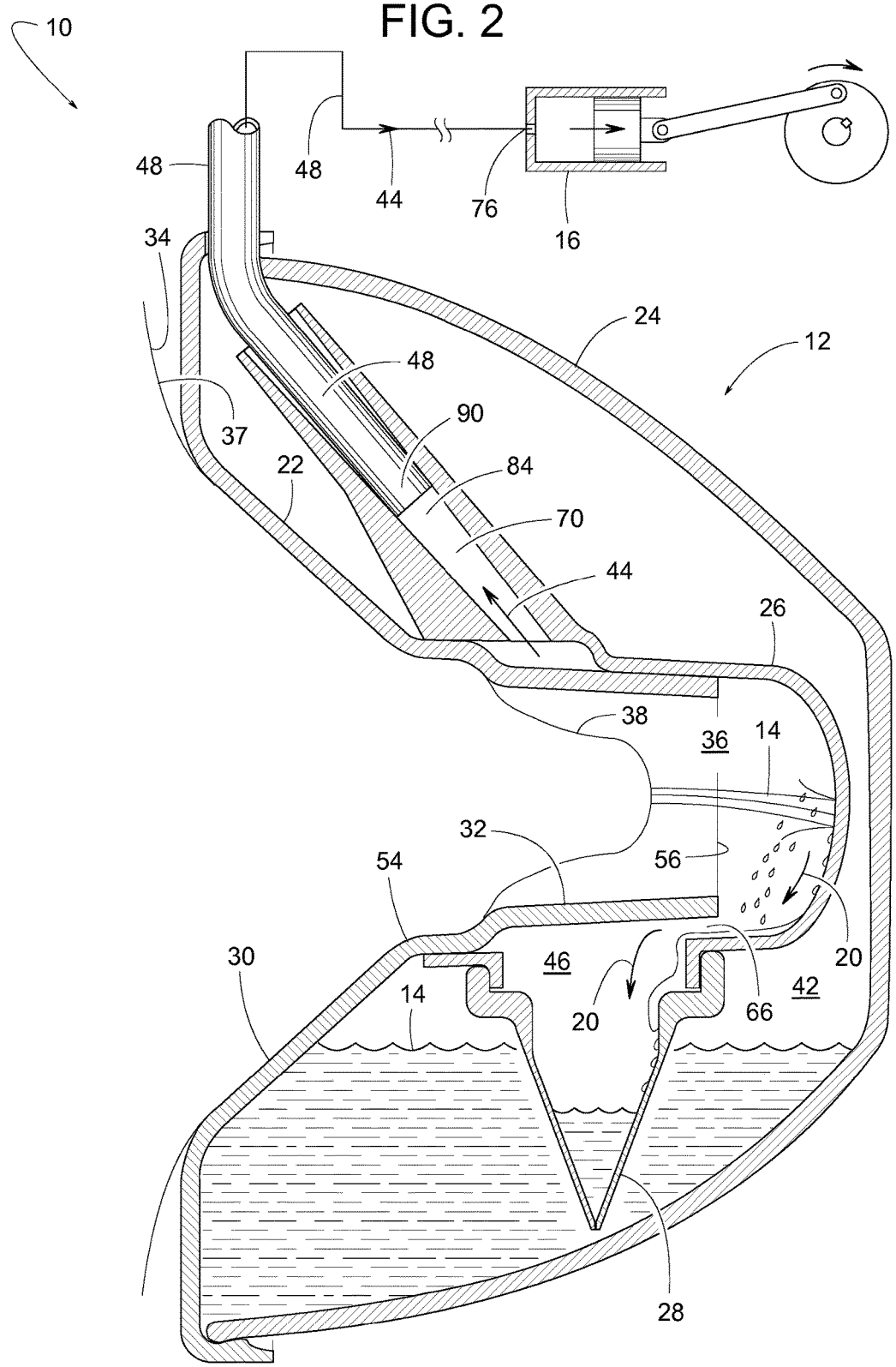
FIG. 2 is a combination schematic diagram and cross-sectional side view similar to FIG. 1 but showing the milk collection device as part of an example breast pump system.

In some examples, system 10 operates in an alternating manner of suction periods and pressurized periods. During suction periods, as shown in FIGS. 2 and 15, vacuum pump 16 applies suction or air at subatmospheric pressure to a remote end 76 of suction tube 48. At least some of the vacuum reaches nipple chamber 36 to draw milk expressed from nipple 38. The expressed milk 14 flows from nipple chamber 36, flows through milk passage 66, and collects at the bottom of charging chamber 46. The negative air pressure produced by vacuum pump 16 creates a first current of air 78 (FIG. 15) that effectively moves from nipple chamber 36 and effectively flows in series through milk passage 66, through charging chamber 46, through air duct 70 (FIGS. 9, 10, 15 and 16), through suction tube 48, and to vacuum pump 16. The terms, "effectively moves" and "effectively flows" means that there is some air movement from an upstream point toward a downstream point, but the air at the upstream point will not necessarily reach the downstream point, due to the travel distance and/or other flow constraints.

Figure 3:
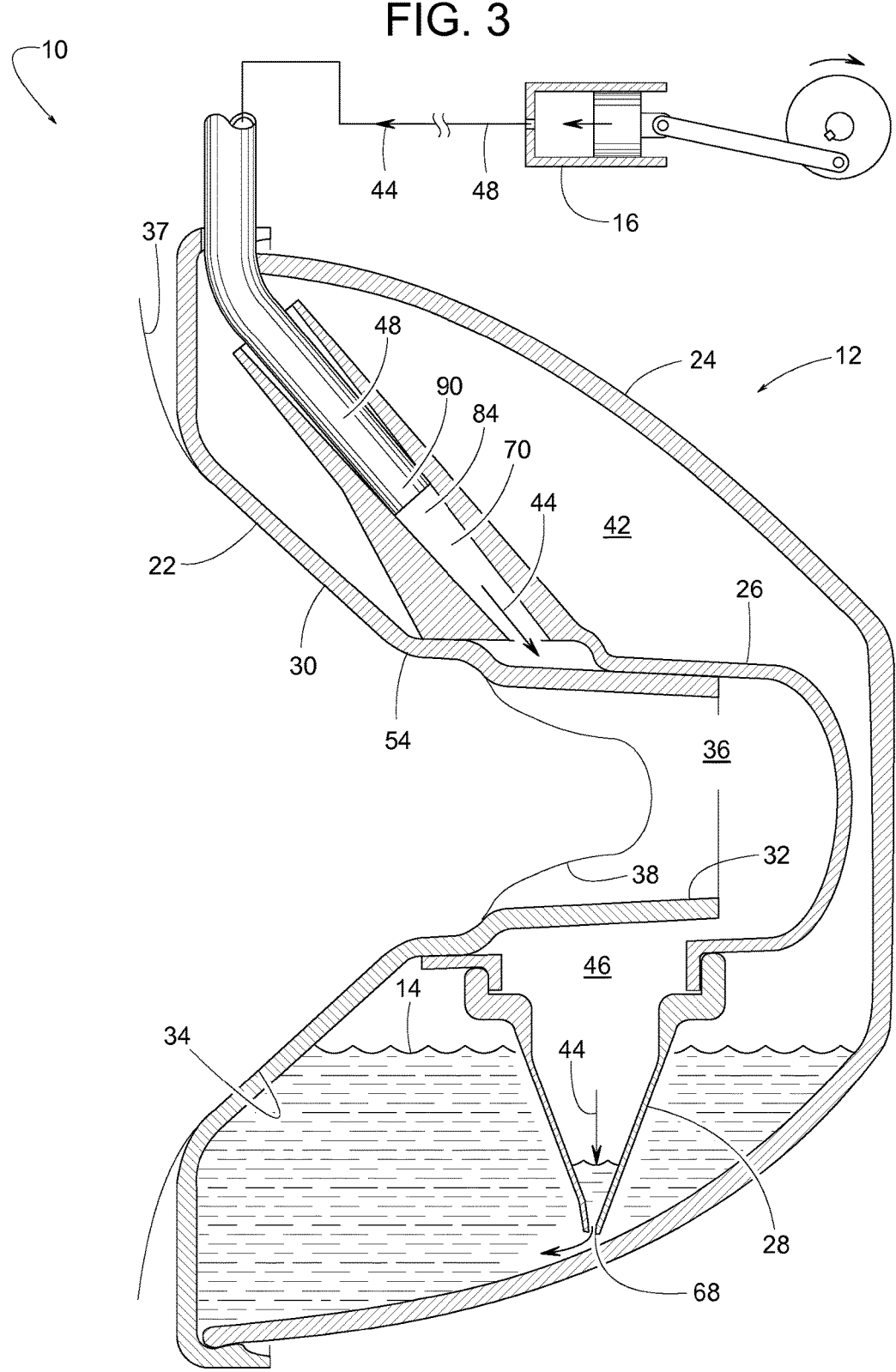
FIG. 3 is a view similar to FIG. 2 but showing the system during a positive pressure period rather than a suction pressure period.
Figure 4:
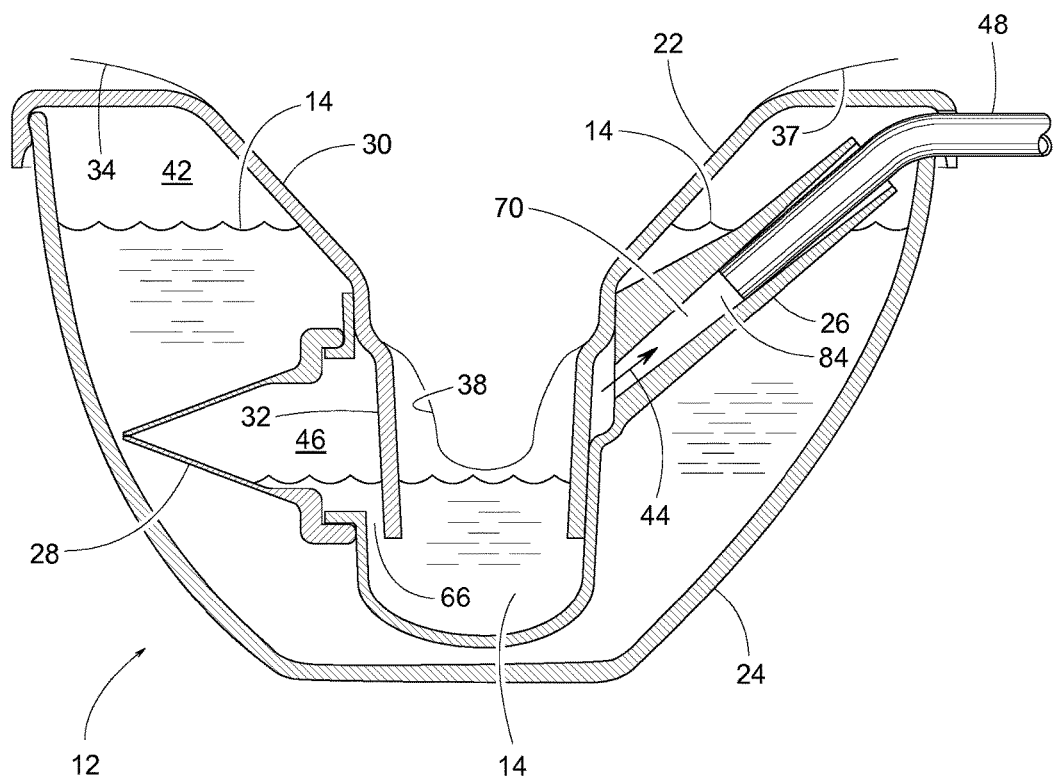
FIG. 4 is a cross-sectional side view of the milk collection device shown in FIGS. 1-3, but showing the device fully tipped over and pointed down.

During pressurized periods, as shown in FIGS. 3 and 16, vacuum pump 16 applies positive air pressure to suction tube 48. The positive pressure creates a second current of air 80 that effectively flows in series through suction tube 48, through air duct 70, through milk passage 66, and into nipple chamber 36. The air pressure in charging chamber 46 forces milk 14 (collected during the previous suction period) from charging chamber 46, down through valve 28, and into storage chamber 42. The air pressure in nipple chamber 36 allows breast 34 to relax prior to the next suction period.

The alternating cycle of suction and pressure is repeated for as long as desired or until storage chamber 42 is filled to some predetermined capacity. Upon completion of the pumping process, any suitable means can be used for transferring collected milk from storage chamber 42 to a bottle or to some other convenient storage container. One example method for transferring milk 14 from storage chamber 42 is to pull suction tube 48 out from within an opening 82 (FIG. 5) between breast receiver 22 and outer shell 24, and then pour collected milk 14 out through opening 82. Another method is to turn milk collection device 12 over (e.g., FIG. 4), remove breast receiver 22 from outer shell 24, and simply pour milk 14 out from shell 24.

Although FIG. 4 is referred to illustrate means for emptying milk 14 collected in storage chamber 42, the primary purpose of FIG. 4 is to show how well device 12 tolerates a completely tipped-over condition while still preventing milk 14 from backflowing into suction tube 48. Device 12 has three features that prevent milk backflow. One, in the tipped-over position, air duct 70 remains elevated above milk passage 66. Two, a circumferential seal 74 (FIG. 12) exists between air duct 70 and milk 14 in nipple chamber 36. Three, air duct 70 connects to charging chamber 46 at two spaced apart openings 86 and 88 (see FIG. 15 and the explanation referencing FIGS. 17, 18 and 19)

Preventing milk 14 from entering suction tube 48 is important for several reasons. Milk droplets or even a milk film trapped inside a narrow suction tube can be very difficult to thoroughly clean and sanitize. If left unclean, the trapped milk might contaminate future milk collections. Also, if milk in suction tube 48 migrates into vacuum pump 16, the milk can be even more difficult to remove and can possibly damage or destroy pump 16. Tolerating such unsanitized conditions is generally unheard of in the fields of medicine and food processing.

Figure 6:
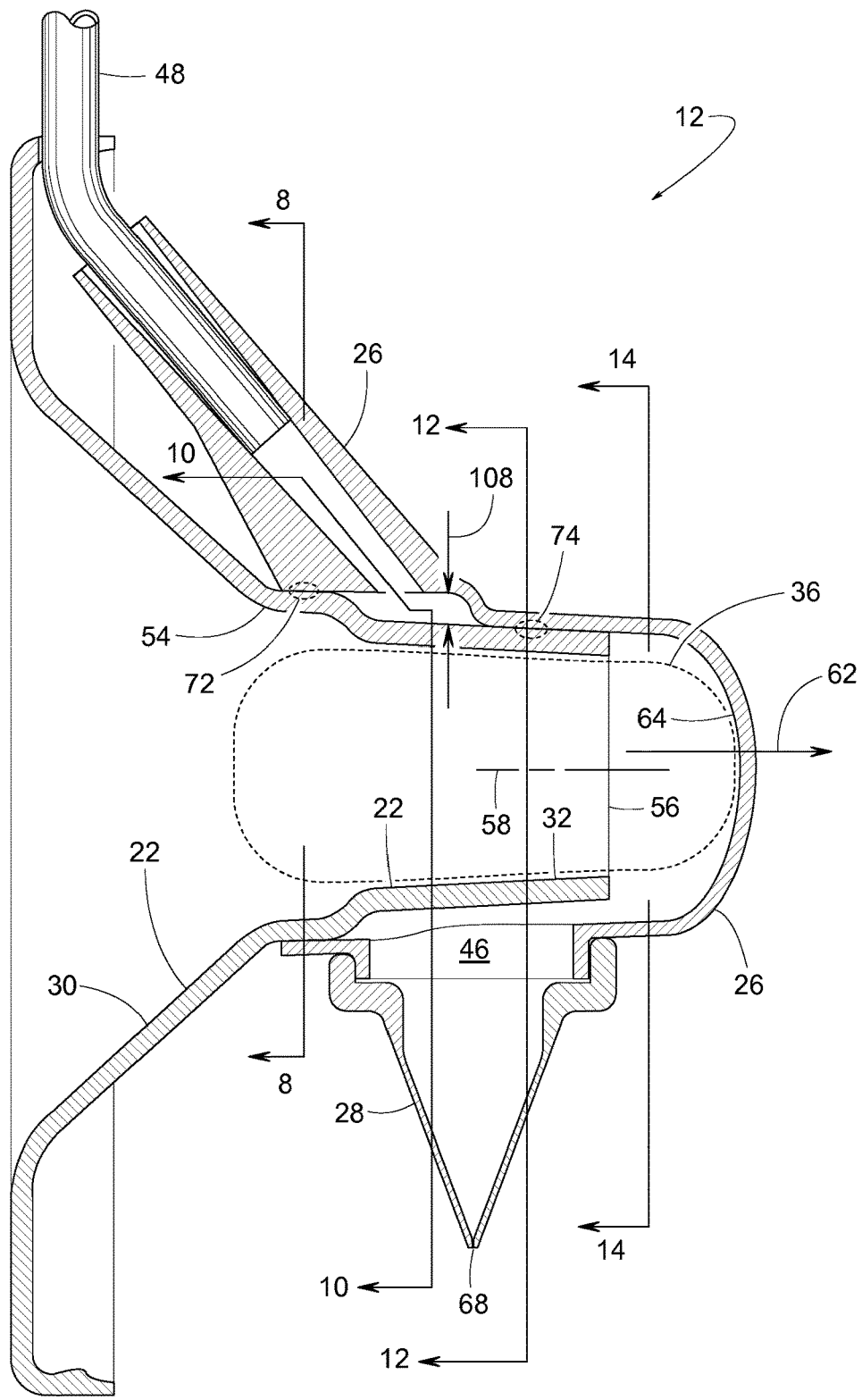
FIG. 6 is a cross-sectional view similar to FIG. 1 but with the outer shell omitted.

FIG. 6 serves as somewhat of an index drawing for a subsequent series of cross-sectional views. The views in the series are shown in sets of two and are identified as FIGS. 7-8, FIGS. 9-10, FIGS. 11-12, and FIGS. 13-14. FIGS. 7-8 show primary sealing interface 72 between an outer diameter of breast receiver 22 and an inner diameter of fluid exchanger 26. Primary sealing interface 72 is a relatively tight seal that extends 360 degrees circumferentially around centerline 58 to isolate localized pressure or vacuum within charging chamber 46 while the surrounding storage chamber 42 is at atmospheric pressure. In some examples, to ensure a positive seal, interface 72 tapers at 3-degrees in a lengthwise direction with reference to centerline 58.

FIGS. 9-10 show one example of air duct 70 connecting vacuum tube 48 in fluid communication with charging chamber 46. In this example, air duct 70 comprises a supply port 84 at a connection end 90 of suction tube 48, a first opening 86 at charging chamber 46, and a second opening 88 at charging chamber 46. To connect tube 48 to supply port 84, connection end 90 of suction tube 48 press-fits into a tapered bore 92 of fluid exchanger 26. A fork 94 (e.g., one path leading to two) in air duct 70 connects supply port 84 in fluid communication with openings 86 and 88. Features 84, 86 and 88 of FIG. 10 correspond respectively to points 84', 86' and 88' of FIG. 18. Features 84, 86 and 88 of FIG. 10 also correspond respectively to points 84", 86" and 88" of FIG. 19.

To apply the "vacuum break" concept illustrated in FIGS. 17 and 18, fork 94 straddles nipple receptacle 36 so that openings 86 and 88 are spaced apart in a lateral direction 96 with the nipple receptacle longitudinal centerline 58 being laterally interposed between openings 86 and 88 (dimensions 98 and 100). In some examples, nipple receptacle 36 is flanked by openings 86 and 88, which means that the nipple's longitudinal centerline 58 is laterally between openings 86 and 88, as shown in FIG. 10. The spaced-apart distance and elevation of openings 86 and 88 can be increased by increasing the diameter of a flange 99 to which valve 28 is attached.

Still referring to FIG. 10, some examples of air duct 70 define a flow path 102 from supply port 84 to first opening 86, wherein a curved section of flow path 102 extends circumferentially an angular distance 104 of at least thirty degrees to avoid having to create an alternate flow path in front of or through nipple chamber 36. In some examples, at least one section 106 of flow path 102 lies within a radial gap 108 between fluid exchanger 26 and the nipple receptacle's outer curved wall surface 52. Upon disassembling device 12 to its disassembled cleaning state (FIG. 5), section 106 of flow path 102 is split apart, which makes flow path 102 and air duct 70 much more accessible for cleaning.

FIGS. 11 and 12 show secondary sealing interface 74 radially between fluid exchanger 26 and the nipple receptacle's outer curved wall surface 52. Secondary sealing interface 74 provides a barrier that prevents milk 14 from flowing directly from nipple chamber 36 to air duct 70. FIG. 11 shows air duct 70 being between primary sealing interface 72 and secondary sealing interface 74.

Primary sealing interface 72 is the more critical seal of the two because primary sealing interface 72 is subjected to an appreciable pressure differential between supply port 84 and storage chamber 42. Secondary sealing interface 74, however, is not as critical because the pressure differential between supply port 84 and nipple chamber 36 is nearly zero. Consequently, in some examples, primary sealing interface 72 is made to be a tighter seal than secondary sealing interface 74. In other words, when breast receiver 22 is snugly inserted into fluid exchanger 26, the radial forces at primary sealing interface 72 is greater than that at secondary sealing interface 74.

It can be important to have primary sealing interface 72 be the dominant seal because when breast receiver 22 is inserted into fluid exchanger 26, something has to "bottom out" first to stop the relative insertion movement of breast receiver 22 into fluid exchanger 26. If secondary sealing surface 74 or distal end 56 abutting domed surface 64 were to be the first parts to bottom out, that might leave some radial clearance or leak path at primary sealing interface 72. Intentionally making primary sealing interface 72 be the first to bottom out, loosens the manufacturing tolerances at other near bottom-out locations, thus increasing assembly reliability, reducing tooling costs, and simplifying manufacturing.

FIGS. 13 and 14 show milk passage 66 between charging chamber 46 and nipple chamber 36. FIGS. 14 and 5 show how an irregular shaped upper flange 110 of valve 28 serves as a means for "clocking" or rotationally aligning valve 28 to fluid exchanger 26. Such alignment can be important to avoid interference between a lower end 112 of valve 28 and outer shell 24. For instance, if valve 28 were rotated ninety degrees (about a vertical axis 114) from the position shown in FIG. 1, the valve's lower end 112 might press up against outer shell 24, whereby outer shell 24 might hold valve 28 open and prevent it from closing.

FIGS. 15 and 16 illustrate an example breast pump method operating during a first suction period (FIGS. 2 and 15) and a second pressure period (FIGS. 3 and 16). FIG. 15 shows during the first period, directing first current of air 78 in a first curved upward direction circumferentially across a first outer convex wall surface 116 of nipple receptacle 32. FIG. 15 also shows during the first period, directing a third current of air 118 in a second curved upward direction circumferentially across the nipple receptacle's first outer convex wall surface 116. FIG. 16 shows during the second period, directing second current of air 80 in a first curved downward direction circumferentially across the nipple receptacle's first outer curved wall surface 116. FIG. 16 also shows during the second period, directing a fourth current of air 120 in a second curved downward direction circumferentially across the nipple receptacle's first outer curved wall surface 116, wherein nipple receptacle 32 is interposed between first current of air 78 and third current of air 118 during the first period, and nipple receptacle 32 is interposed between second current of air 80 and fourth current of air 120 during the second period.

FIGS. 17 and 18 illustrates the concept of a vacuum breaker as a means for preventing a liquid 122 from backflowing up to a suction source 124. Liquid 122 only reaches suction source 124 when both openings 86' and 88' are submerged in liquid 122, as shown in FIG. 17. If only one opening 86' is submerged and the other opening 88' is exposed to air 44, as shown in FIG. 18, air 44 readily supplies the volume drawn in by suction source 124.

Through a given opening, air can flow about thirty times easier than water. Consequently, only a slight pressure differential is needed for air 44 to rush through opening 88' to suction source 124. That slight pressure differential creates only a slight pressure head 126 that is unable to lift liquid 122 from opening 86' to suction source 124.

FIG. 19 provides another example of illustrating a vacuum breaker concept. This example involves the use of a residential water line 128, an outdoor faucet 130, a simplified vacuum breaker 132, and a garden hose 134 partially submerged in a bucket 136 of contaminated water 138. In this example, if unusual adverse conditions create a vacuum in water line 128, clean outdoor air 44 rather than contaminated water 138 will be drawn into water line 128.

Figure 20:
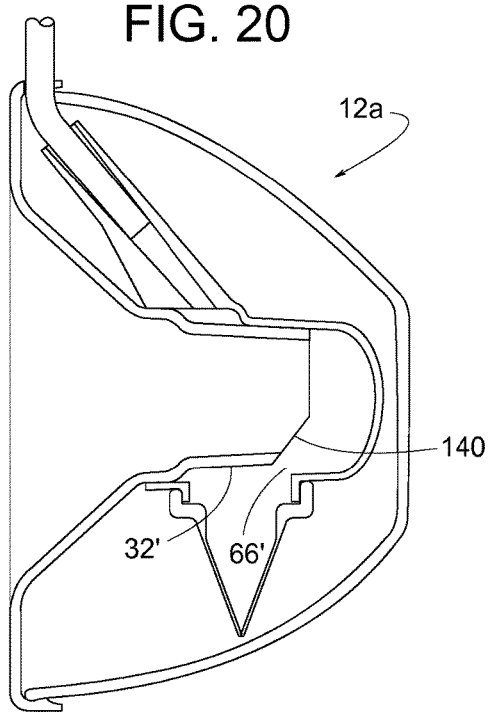
FIG. 20 is a cross-sectional view similar to FIG. 1 but showing another example milk collection device constructed in accordance with the teachings disclosed herein.

FIGS. 20, 21 and 22 show various design modifications. FIG. 20 shows an altered milk passage 66' created by a beveled edge 140 at the end of a nipple receptacle 32'. FIG. 21 shows an altered milk passage 66" created by a notched edge 142 at the end of a nipple receptacle 32". FIG. 22 shows that a stubbier fluid exchanger 26' and a less protruding outer shell 24' can be used when air duct 4 curves around the sides of the nipple receptacle rather than in front of it. The stubbier fluid exchanger 26' also reduces the effective volume of charging chamber 46, which can be beneficial when using certain low displacement vacuum pumps.

Figure 23:
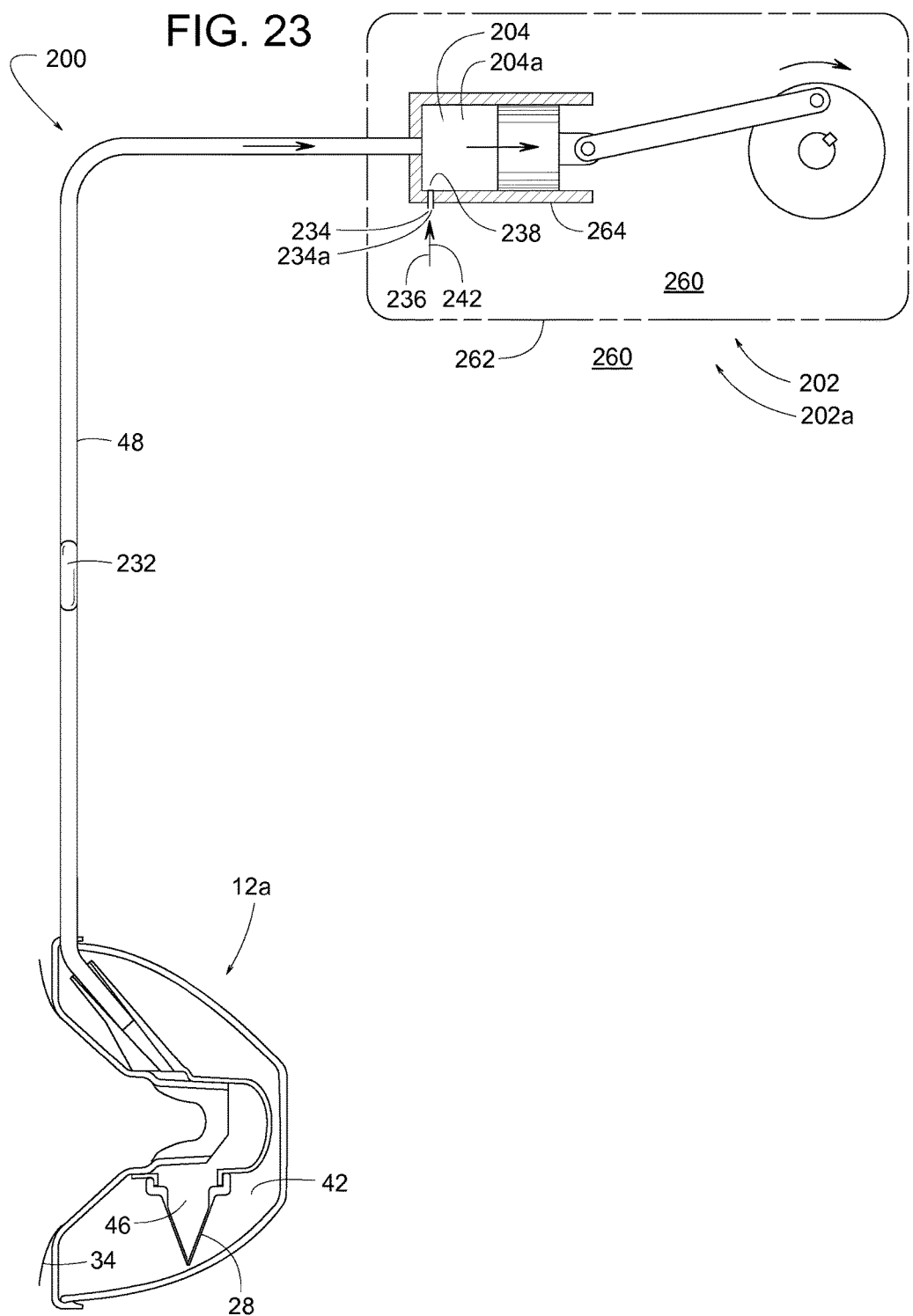
FIG. 23 is a combination schematic diagram and cross-sectional side view similar to FIG. 2 but another example breast pump system constructed in accordance with the teachings disclosed herein, and showing the system during a negative pressure period.
Figure 24:
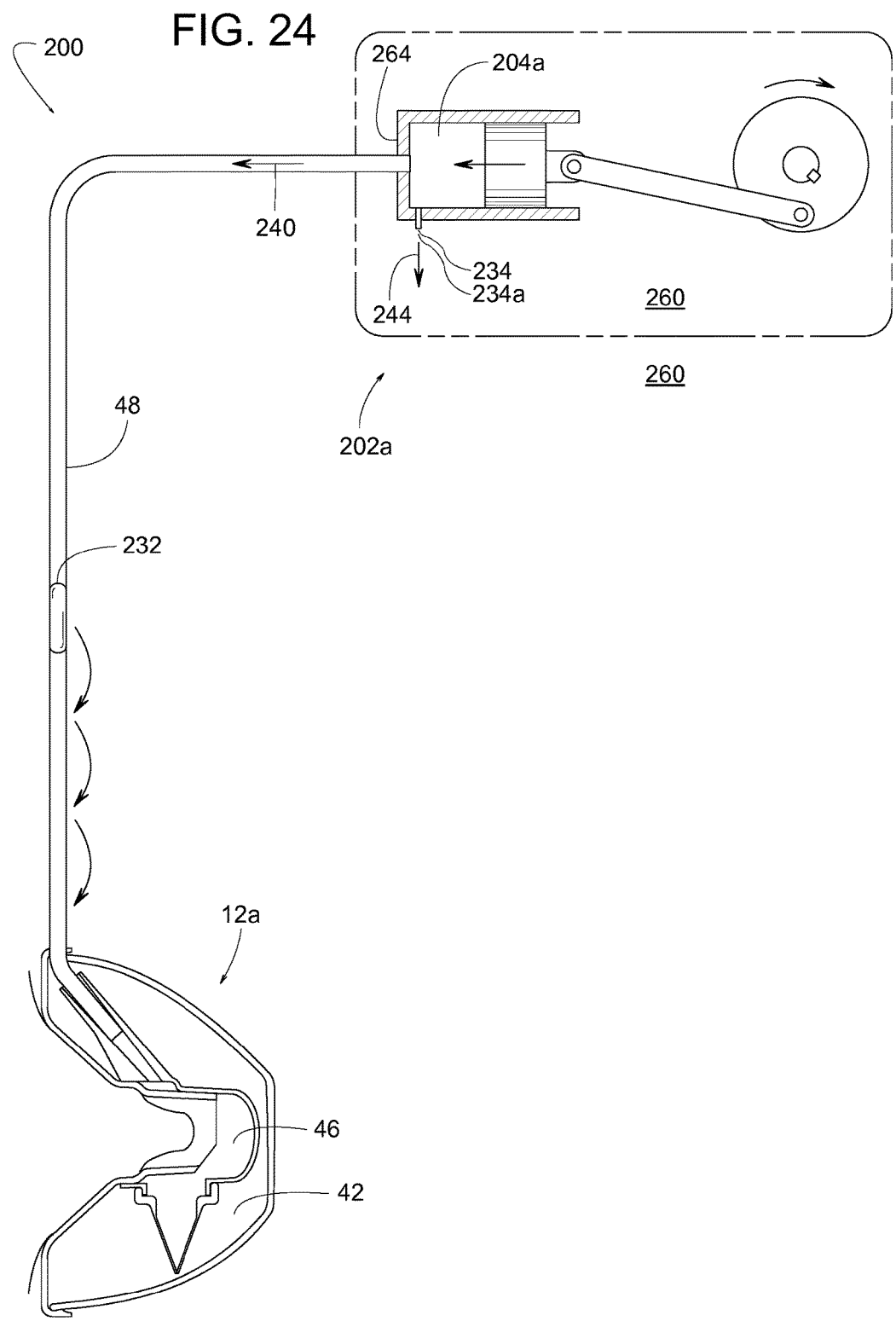
FIG. 24 is a combination schematic diagram and cross-sectional side view similar to FIG. 23 but showing the system during a positive pressure period.
Figure 25:
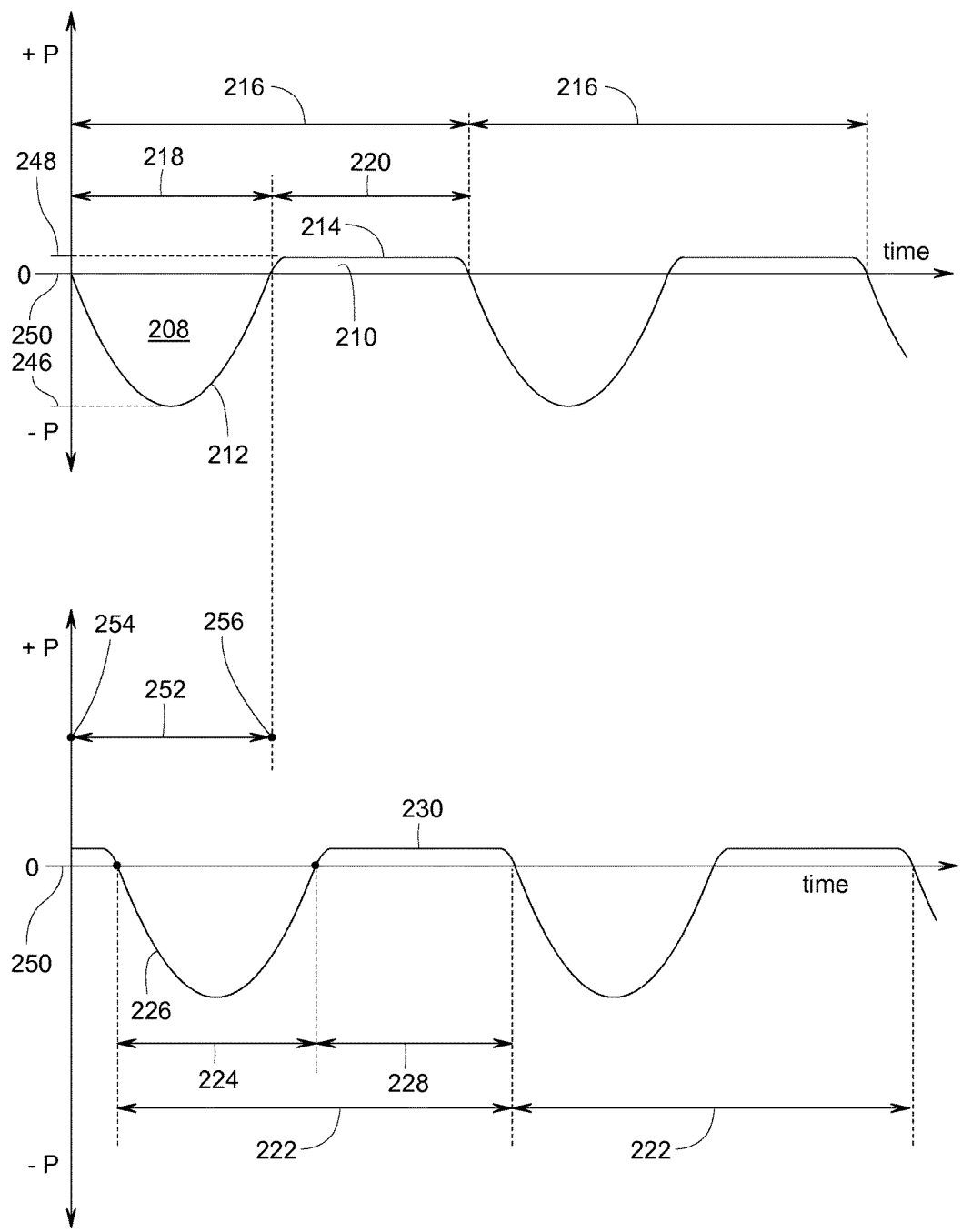
FIG. 25 is a graph showing various plots of pressure varying over time.

FIGS. 23 and 24 show an example breast pump system 200 comprising a vacuum pump system 202 (e.g., pump system 202a, 202b and 202c) and a milk collection device (e.g., milk collection device 12a). Suction tube 48 connects an air chamber 204 of pump system 200 to a charging chamber 46 of milk collection device 12a. Referring to FIGS. 23, 24 and 25, pump system 202 operates cyclically between a negative pressure state 208 (FIG. 23) and a positive pressure state 210 (FIG. 24). Air chamber 46 is at a first negative gage pressure 212 when pump system 202 is in negative pressure state 208, and air chamber 46 is at a first positive gage pressure 214 when pump system 202 is in positive pressure state 210. Such a cyclical operating mode provides a plurality of pump cycles 216. Each pump cycle 216 has a negative pressure period 218 corresponding to negative pressure state 208 and a positive pressure period 220 corresponding to positive pressure state 210. Pump system 202 subjects charging chamber 46 of milk collection device 12a to a cyclical operating state comprising a plurality of milk cycles 222. Each milk cycle 222 includes a suction period 224 at a second negative gage pressure 226 and a release period 228 at second positive gage pressure 230.

In the event that a milk droplet 232 accidentally enters suction tube 48, vacuum pump system 202 includes a supplementary opening 234 that cyclically injects a tiny volume of atmospheric air 236 that pushes milk droplet 232 back toward milk collection device 12a. An incremental tiny volume of air 236 is injected with each pump cycle, so milk droplet 232 moves incrementally back toward milk collection device 12a. In some examples, supplementary opening 234 (e.g., supplementary openings 234a and 234c) injects air 236 directly into an air chamber 204 (e.g., air chambers 204a and 204c) of pump system 202. In other examples (FIGS. 26 and 27), supplementary opening 234b injects air 236 into tube 48 at a point 238 proximate to and in fluid communication with air chamber 204.

In some examples, to ensure that airflow through supplementary opening 234 has no more than an inconsequential negative impact on the normal operation of breast pump system 200, the airflow resistance of supplementary opening 234 is at least ten times greater than the airflow resistance of suction tube 48. Consequently, in some examples, pump system 202 cyclically forces a main current of air 240 to flow at least momentarily and locally through suction tube 48, wherein the mass flow rate of main current of air 240 is at least ten times greater than the mass flow rate of an incoming current of air 242 flowing through supplementary opening 234. To ensure that the net incoming/outgoing airflow through supplementary opening 234 urges milk droplet 232 away from pump system 202 rather than toward it, incoming current of air 242 flowing through supplemental opening 234 during negative pressure period 218 flows at an incoming mass flow rate that is greater than an outgoing mass flow rate of an outgoing current of air 244 during positive pressure period 220. The flow of main current of air 240 is sometimes momentary and localized due valve 28 and breast 34 mostly preventing air from freely backflowing into suction tube 48, so the main current of air 240 is sometimes due to air equalizing in pressure along the length of suction tube 48.

In some examples, the incoming mass flow rate of incoming current of air 242 is greater than the outgoing mass flow rate of outgoing current of air 244 because the pressure differential across supplementary opening 234 is greater during negative pressure period 218 than during positive pressure period 220, as shown in FIG. 25. More specifically, in some examples, the air in air chamber 204 reaches a minimum absolute pressure 246 while vacuum pump system 202 is in the negative pressure state 208, the air in air chamber 204 reaches a maximum absolute pressure 248 while vacuum pump system 202 is in positive pressure state 210, and the ambient air pressure 250 is closer to the maximum absolute pressure 248 than to the minimum absolute pressure 246. Check valve 28 opening to release fluid from charging chamber 46 to storage chamber 42 is what limits the maximum absolute pressure 248 within charging chamber 46. In some examples, the maximum absolute pressure 248 within charging chamber 46 is a function of fluid flow resistance and the liquid head of milk in charging chamber 46.

In some examples, incoming current of air 242 flows through supplementary opening 234 by way of at least one continuous air injection period 252 extending from a commencement time 254 to a termination time 256, wherein commencement time 254 is prior to suction period 224 of a given milk cycle 222, and termination time 256 is prior to the completion of suction period 224 of the given milk cycle 222. Such a time delay between suction period 224 and air injection period 252 is achieved, in some examples, by providing suction tube 48 with appreciable flow resistance (e.g., providing tube 48 with a ⅛" or otherwise relatively small inner diameter 258). The time delay serves as a preemptive measure by ensuring that milk-opposing injected air 236 enters tube 48 prior to negative pressure in charging chamber 46 acting upon and possibly drawing milk droplet 232 into tube 48.

In some examples, as shown in FIGS. 26 and 27, vacuum pump system 202b includes a tube section 48' (e.g., an integral extension of suction tube 48) extending between suction tube 48 and air chamber 204. Tube section 48' connects suction tube 48 in fluid communication with air chamber 204. In this example, tube section 48' includes supplementary opening 234b, which connects an exterior 264 of pump system 202b in fluid communication with air chamber 204. In some examples, exterior 264 of vacuum pump system 202b is exposed to ambient air 260 at substantially ambient air pressure. In some examples, one or more parts of vacuum pump system 202b are disposed within a housing 262 that is not hermetically sealed, whereby ambient air 260 at substantially ambient air pressure is found both within and outside of housing 262. In some examples, exterior 264 is between air chamber 204 and housing 262. In some examples, housing 262 is between exterior 264 and air chamber 204.

In some examples, tube section 48' and suction tube 48 are substantially equal to each other with respect to an outer diameter 266, inner diameter 258, and a material composition (e.g., vinyl). In some examples, supplementary opening 234 is closer to air chamber 204 than to milk collection device 12a to increase the likelihood that incoming current of air 242 is injected between air chamber 204 and milk droplet 232. In some examples, suction tube 48 has inner diameter 258 across an open tube area 268 within suction tube 48, and open tube area 268 is at least ten times greater in area than supplementary opening 234 to ensure that the volume flow rate of incoming current of air 242 has no more than an inconsequential negative impact on the pump system's operating efficiency. For that same reason, in some examples, vacuum pump system 202 has a volumetric pump displacement that is at least ten times greater than the volume of the incoming current of air 242 during one air injection period 252.

Figure 28:
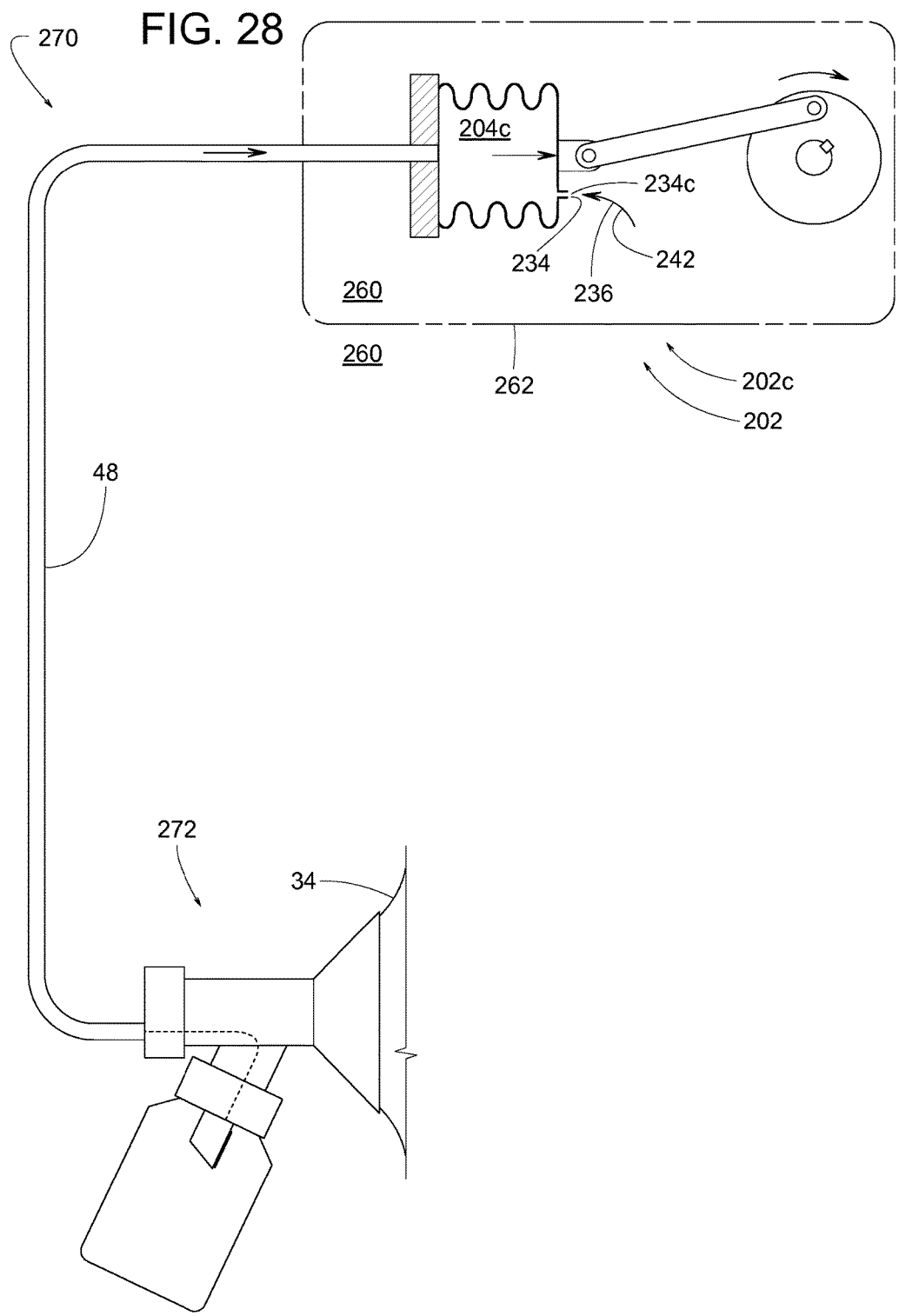
FIG. 28 is a combination schematic diagram and cross-sectional side view similar to FIG. 23 but another example breast pump system constructed in accordance with the teachings disclosed herein, and showing the system during a negative pressure period.
Figure 29:
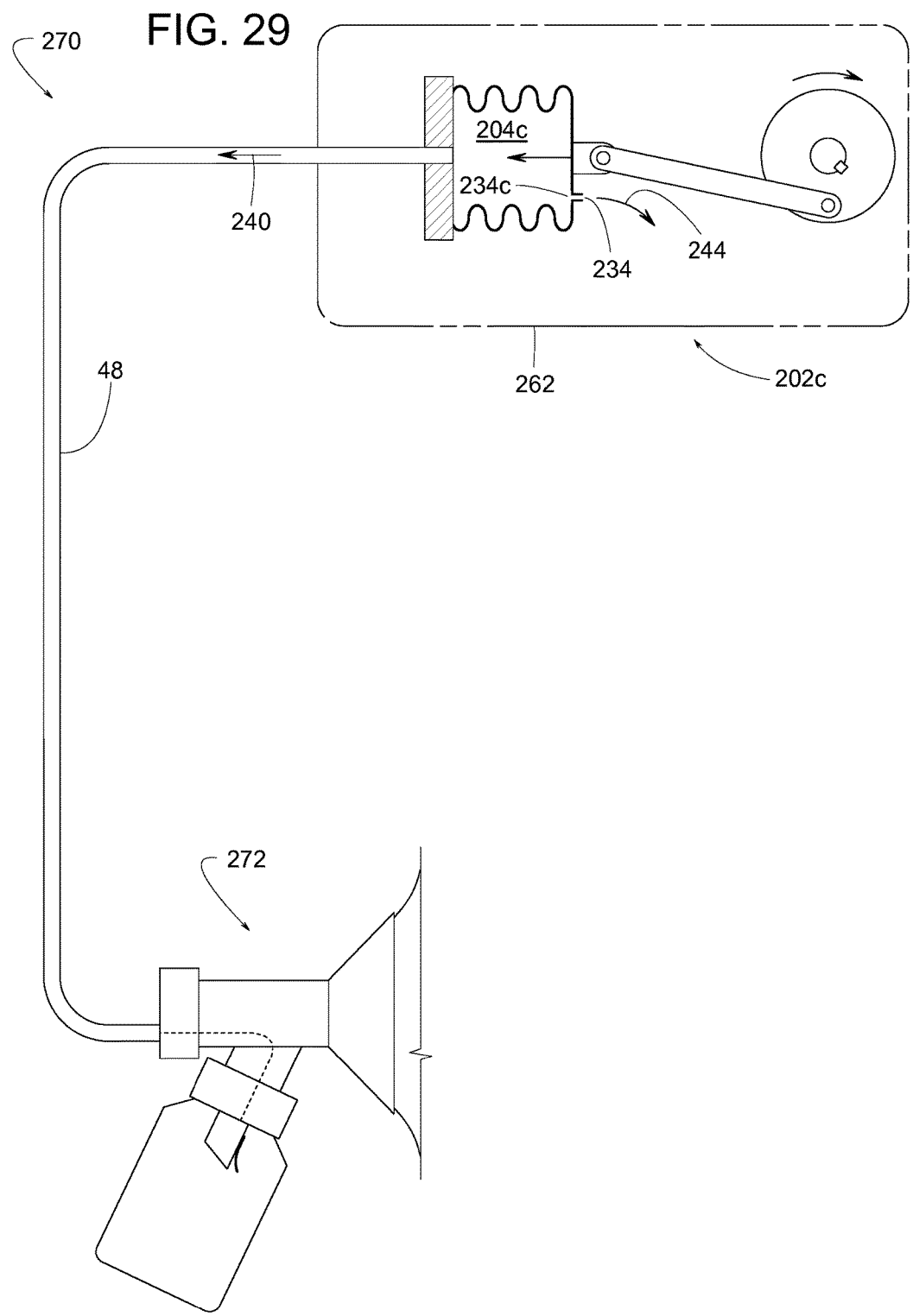
FIG. 29 is a combination schematic diagram and cross-sectional side view similar to FIG. 28 but showing the system during a positive pressure period.

FIGS. 28 and 29 show an example breast pump system 270 comprising a bellows-style vacuum pump system 202c and a MEDELA style milk collection device 272. In this example, supplementary opening 234c connects air chamber 204c in fluid communication with exterior atmospheric air 260 to convey incoming current of air 242 during negative pressure period 218 (FIG. 28) and to convey outgoing current of air 244 during positive pressure period 220 (FIG. 29).

Figure 30:
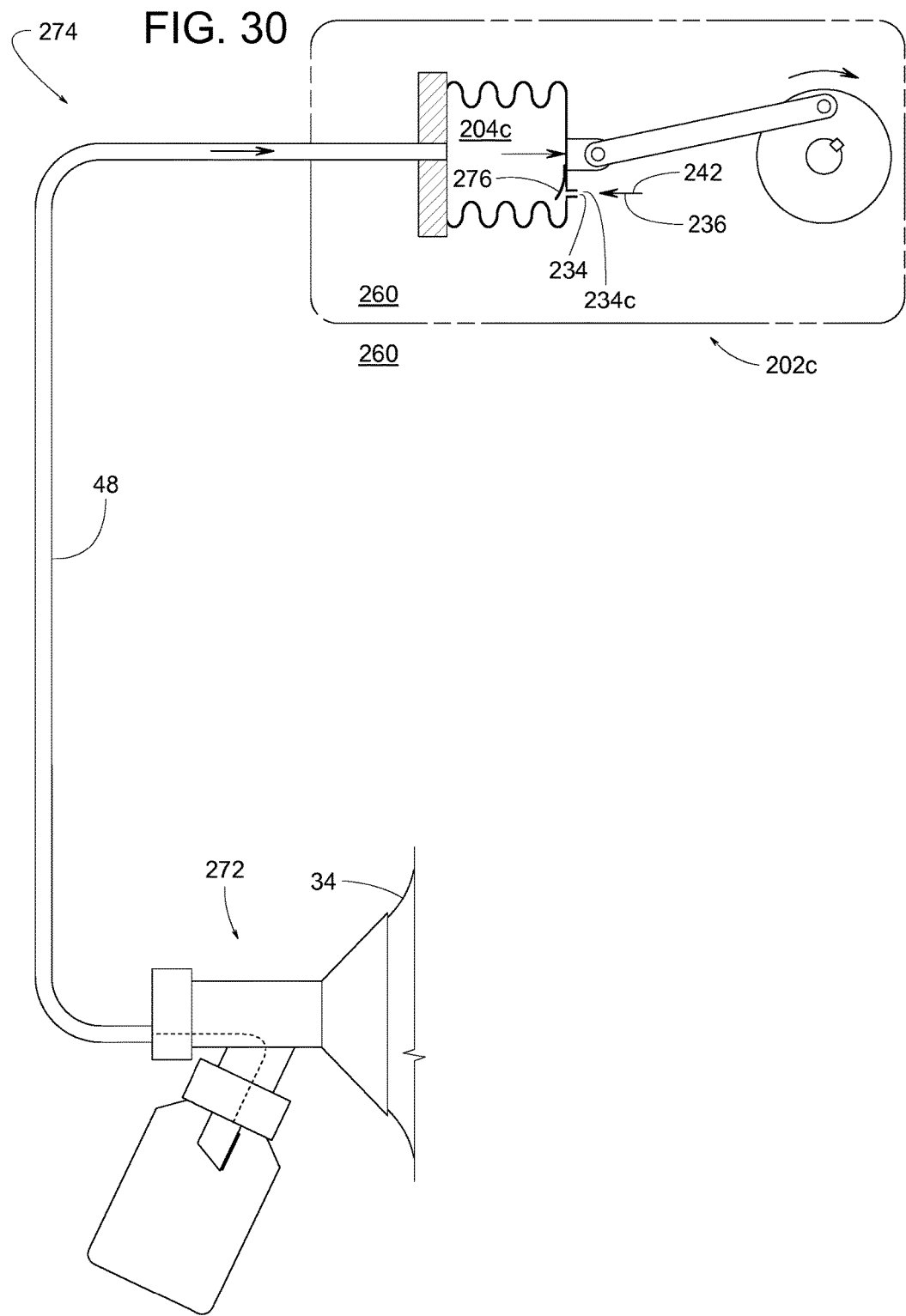
FIG. 30 is a combination schematic diagram and cross-sectional side view similar to FIG. 28 but showing the system with the addition of a reed check valve that is open during a negative pressure period.
Figure 31:
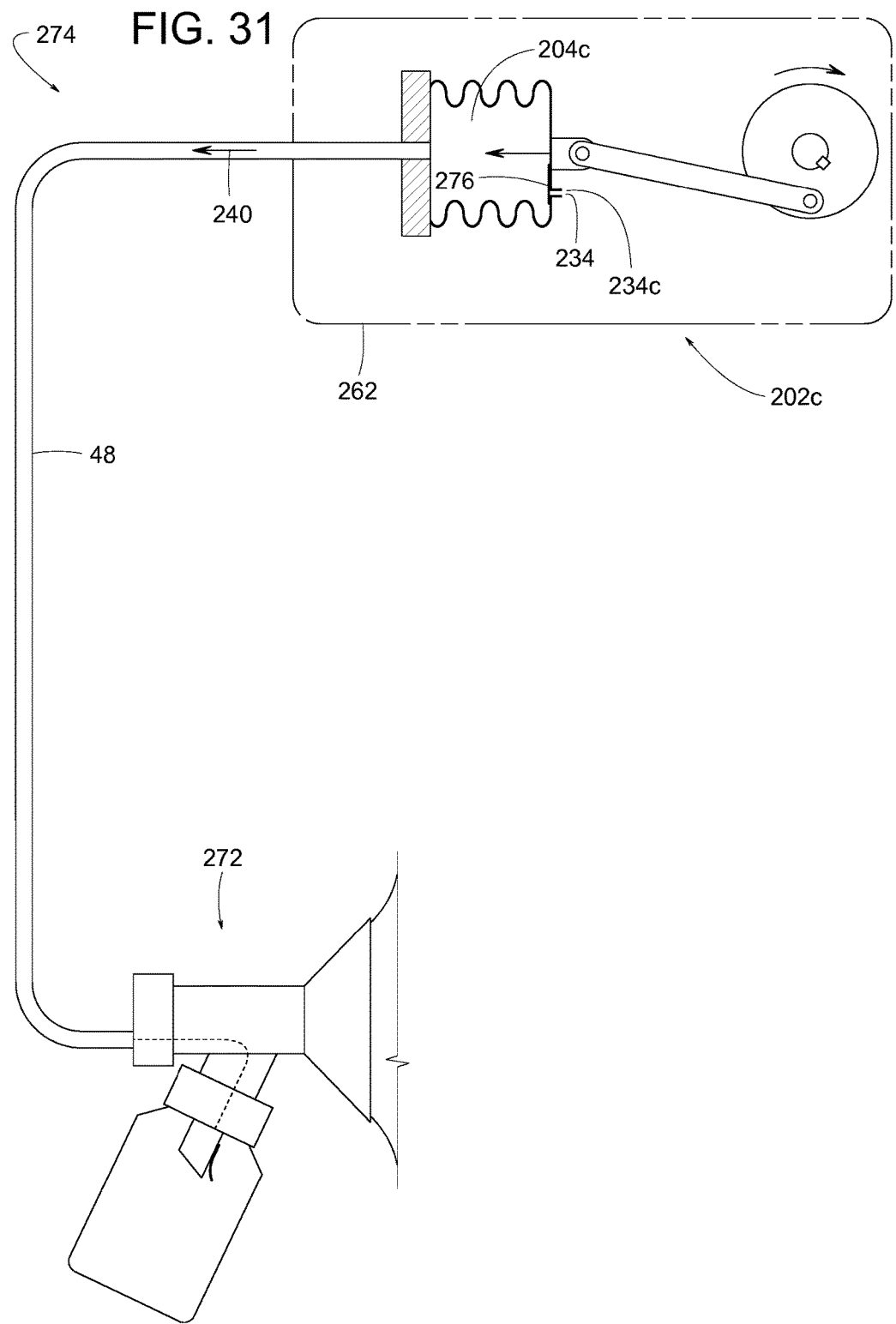
FIG. 31 is a combination schematic diagram and cross-sectional side view similar to FIG. 30 but showing reed check valve closed during a positive pressure period.

FIGS. 30 and 31 show an example breast pump system 274 with an added reed valve 276 for minimizing or eliminating outgoing current of air 244. FIG. 30 shows system 274 during negative pressure period 218, and FIG. 31 shows system 274 during positive pressure period 220.

For further clarification, the term, "suction tube" refers to any conduit having a tubular wall of sufficient thickness, stiffness, and/or strength to convey air at subatmospheric pressure. In some examples, suction tube 48 is more flexible than outer shell 24, breast receiver 22, and/or fluid exchanger 26. Such tube flexibility makes tube 48 easier to use and fit to fluid exchanger 26. The term, "coupled to" refers to two members being connected either directly without an intermediate connecting piece or being connected indirectly via an intermediate connecting piece between the two members. The term, "coupled to" encompasses permanent connections (e.g., bonded, welded, etc.), seamless connections (e.g., the two members are of a unitary piece), and separable connections. The term, "opening" of a fluid pathway refers to a cross-sectional area through which fluid is directed to flow in a direction generally perpendicular to the area as guided by the fluid pathway. The term, "radial gap" refers to clearance as measured in a direction perpendicular to longitudinal centerline 58. The terms, "negative pressure," "subatmospheric pressure," and "vacuum" all refer to a pressure that is less than atmospheric pressure. The term, "positive pressure," refers to a pressure that is greater than atmospheric pressure. The term, "gage pressure" refers to pressure relative to atmospheric air pressure. Storage chamber 42 is not necessarily for long term storage but rather for collecting and temporarily storing milk 14 as the lactating woman is expressing milk. In some examples, milk collection device 12 includes a slot-and-key 144 alignment feature (FIG. 8) that establishes a certain desired rotational alignment (about longitudinal centerline 58) between fluid exchanger 26 and breast receiver 22. In some examples, the positive pressure within air chamber 204 is only sufficiently positive to force air lightly through suction tube 48 leading from vacuum pump system 202 to milk collection device 12a. The term, "air flow resistance," as it relates to an airway, is defined as a ratio of a numerator over a denominator, wherein the numerator equals one, and the denominator is the volumetric flow rate in SCFM of air passing through the airway for a given 1 psi pressure differential across the airway. SCFM (standard cubic feet per minute) is the volumetric flow rate of air corrected to standardized conditions of temperature (70 degrees Fahrenheit), pressure (14.7 psia) and relative humidity (0%). In some examples, the supplementary opening is at least ten times more restrictive to airflow than the suction tube for a given applied pressure differential of 1 psi. The expression, "complementary opening being closer to the air chamber than to the milk collection device," refers to linear distances being measured when the air chamber and the milk collection device are at their maximum separation distance as limited by the length of the suction tube extending between the air chamber and the milk collection device. The expression, "the point is closer to the air chamber in the vacuum pump system than to the charging chamber in the milk collection device," refers to linear distances being measured when the vacuum pump system and the milk collection device are at their maximum separation distance as limited by the length of the suction tube extending between the vacuum pump system and the milk collection device. In some examples, the supplementary openings disclosed herein are adapted for use with FREEMIE style breast pump systems, wherein FREEMIE is a registered trademark of DAO Health of Sacramento, Calif. In some examples, the supplementary openings disclosed herein are adapted for use with MEDELA style breast pump systems, wherein MEDELA is a registered trademark of Medela Holding AG of Barr, Switzerland.

Although the invention is described with respect to a preferred embodiment, modifications thereto will be apparent to those of ordinary skill in the art. The scope of the invention, therefore, is to be determined by reference to the following claims.

The invention claimed is:

1. A breast pump system that uses air for assisting a lactating woman in collecting milk expressed by a breast of the lactating woman, the breast pump system having an exterior exposed to ambient air, the breast pump system comprising:
   a vacuum pump system defining an air chamber, the vacuum pump system being operable cyclically in a negative pressure state and a positive pressure state, the air in the air chamber being at a first negative pressure when the vacuum pump system is in the negative pressure state, the air in the air chamber being at a first positive pressure when the vacuum pump system is in the positive pressure state, the vacuum pump system defining a supplementary opening that connects the exterior in fluid communication with the air chamber;
   a milk collection device being configured to fittingly receive the breast of the lactating woman; and
   a suction tube connecting the air chamber in fluid communication with the milk collection device, the suction tube having a first airflow resistance, the supplementary opening having a second airflow resistance, and the second airflow resistance being at least ten times greater than the first airflow resistance.

2. The breast pump system of claim 1, wherein the vacuum pump system has a cyclical operating mode comprising a plurality of pump cycles, each cycle of the plurality of pump cycles having a negative pressure period and a positive pressure period, the vacuum pump system being in the negative pressure state during the negative pressure period, the vacuum pump system being in the positive pressure state during the positive pressure period; the breast pump system further comprising:
an incoming current of air flowing at an incoming mass flow rate through the supplementary opening during the negative pressure period; and
an outgoing current of air flowing at an outgoing mass flow rate through the supplementary opening during the positive pressure period, the incoming mass flow rate being greater than the outgoing mass flow rate.

3. The breast pump system of claim 1, wherein the ambient air is at an ambient air pressure, the air in the air chamber reaches a minimum absolute pressure while the vacuum pump system is in the negative pressure state, the air in the air chamber reaches a maximum absolute pressure while the vacuum pump system is in the positive pressure state, and the ambient air pressure is closer to the maximum absolute pressure than to the minimum absolute pressure.

4. The breast pump system 1, wherein the milk collection device defines a charging chamber, the charging chamber having a cyclical operating state comprising a plurality of milk cycles, each milk cycle of the plurality of milk cycles having a suction period and a release period, the air in the charging chamber being at second negative pressure during the suction period, the air in the charging chamber being at a second positive pressure during the release period, the incoming current of air flowing through the supplementary opening having at least one continuous air injection period extending from a commencement time to a termination time, the commencement time being prior to the suction period of a given milk cycle of the plurality of milk cycles, the termination time being prior to a completion of the suction period of the given milk cycle.

5. The breast pump system of claim 1, wherein the vacuum pump system includes a tube section extending between the suction tube and the air chamber, the tube section connecting the suction tube in fluid communication with the air chamber, the tube section defining the supplementary opening that connects the exterior in fluid communication with the air chamber.

6. The breast pump system of claim 1, wherein the vacuum pump system includes a tube section extending between the suction tube and the air chamber, the tube section connecting the suction tube in fluid communication with the air chamber, the tube section defining the supplementary opening that connects the exterior in fluid communication with the air chamber, the tube section and the suction tube being substantially equal to each other with respect to an outer diameter, an inner diameter, and a material composition.

7. The breast pump system of claim 1, wherein the supplementary opening is closer to the air chamber than to the milk collection device.

8. The breast pump system of claim 1, wherein the suction tube has an inner diameter across an open tube area within the suction tube, and the open tube area is at least ten times greater than the supplementary opening.

9. The breast pump system of claim 1, further comprising a main current of air flowing at least momentarily through the suction tube, the main current of air being at mass flow rate that is at least ten times greater than the incoming current of air flowing through the supplementary opening.

10. A breast pump system that uses air for assisting a lactating woman in collecting milk expressed by a breast of the lactating woman, the breast pump system having an exterior exposed to ambient air, the breast pump system comprising:
a vacuum pump system defining an air chamber and a supplementary opening that connects the exterior in fluid communication with the air chamber, the vacuum pump system having a cyclical operating mode comprising a plurality of pump cycles, each pump cycle of the plurality of pump cycles having a negative pressure period and a positive pressure period, the air in the air chamber being at a first negative pressure during the negative pressure period, the air in the air chamber being at a first positive pressure during the positive pressure period;
a milk collection device defining a charging chamber, the milk collection device being configured to engage the breast of the lactating woman;
a suction tube connecting the air chamber in fluid communication with the charging chamber of milk collection device;
an incoming current of air flowing at an incoming mass flow rate through the supplementary opening during the negative pressure period; and
an outgoing current of air flowing at an outgoing mass flow rate through the supplementary opening during the positive pressure period, the incoming mass flow rate being greater than the outgoing mass flow rate.

11. The breast pump system 10, wherein the milk collection device has a cyclical operating state comprising a plurality of milk cycles, each milk cycle of the plurality of milk cycles has a suction period and a release period, the air in the charging chamber being at second negative pressure during the suction period, the air in the charging chamber being at a second positive pressure during the release period, the incoming current of air flowing through the supplementary opening having at least one continuous air injection period having a commencement time and a termination time, the commencement time being prior to the suction period of a given milk cycle of the plurality of milk cycles, the termination time being prior to a completion of the suction period of the given milk cycle.

12. The breast pump system of claim 10, wherein the vacuum pump system includes a tube section extending between the suction tube and the air chamber, the tube section connecting the suction tube in fluid communication with the air chamber, the tube section defining the supplementary opening that connects the exterior in fluid communication with the air chamber.

13. The breast pump system of claim 10, wherein the vacuum pump system includes a tube section extending between the suction tube and the air chamber, the tube section connecting the suction tube in fluid communication with the air chamber, the tube section defining the supplementary opening that connects the exterior in fluid communication with the air chamber, the tube section and the suction tube being substantially equal to each other with respect to an outer diameter, an inner diameter, and a material composition.

14. The breast pump system of claim 10, wherein the supplementary opening is closer to the air chamber than to the milk collection device.

15. The breast pump system of claim 10, wherein the suction tube has an inside diameter across an open tube area within the suction tube, and the open tube area is at least ten times greater than the supplementary opening.

16. The breast pump system of claim 10, further comprising a main current of air flowing at least momentarily through the suction tube, the main current of air reaching a mass flow rate that is at least ten times greater than the incoming current of air flowing through the supplementary opening.

17. A breast pump method that involves the use of at least one of a vacuum pump system having an exterior exposed to ambient air, a lactating woman having a breast for expressing milk, an air chamber defined within the vacuum pump system, a milk collection device that fittingly receives the breast, and a charging chamber defined within the milk collection device, a suction tube connecting the air chamber in fluid communication with the charging chamber, the breast pump method comprising:
   during a suction period that extends continuously from a start time to an end time, continuously maintaining air within the charging chamber at a subatmospheric pressure; and
   during a continuous air injection period, injecting ambient air to a point that is in fluid communication with the air chamber of the vacuum pump system, the continuous air injection period having a commencement time and a termination time, the commencement time being prior to the start time of the suction period, and the termination time being prior to the end time of the suction period.

18. The breast pump method of claim 17, wherein the point is closer to the air chamber in the vacuum pump system than to the charging chamber in the milk collection device.

19. The breast pump method of claim 17, further comprising:
   a localized current of air flowing periodically through the suction tube, and
   an incoming current of air periodically flowing from the exterior of the vacuum pump system to the point that is in fluid communication with the air chamber of the vacuum pump system, wherein the localized current of air flows at least momentarily at a mass flow rate that is at least ten times greater than that of the incoming current of air.

20. The breast pump method of claim 17, wherein the point is within the suction tube.

* * * * *